US012751658B2

(12) United States Patent
Jeong et al.

(10) Patent No.: US 12,751,658 B2
(45) Date of Patent: Oct. 6, 2026

(54) SKIN-PREPARATION-FREE, STRETCHABLE MICRONEEDLE ADHESIVE PATCHES FOR HIGHLY RELIABLE ELECTROPHYSIOLOGICAL MONITORING

(71) Applicant: Korea Advanced Institute of Science and Technology, Daejeon (KR)

(72) Inventors: Jae-Woong Jeong, Daejeon (KR); Heesoo Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 118 days.

(21) Appl. No.: 18/810,553

(22) Filed: Aug. 21, 2024

(65) Prior Publication Data

US 2025/0268502 A1 Aug. 28, 2025

(30) Foreign Application Priority Data

Feb. 27, 2024 (KR) ........................ 10-2024-0028054

(51) Int. Cl.
*A61B 5/259* (2021.01)
*A61B 5/00* (2006.01)
(Continued)

(52) U.S. Cl.
CPC ............ *A61B 5/259* (2021.01); *A61B 5/0004* (2013.01); *A61B 5/262* (2021.01); *A61B 5/296* (2021.01);
(Continued)

(58) Field of Classification Search
CPC ....... A61B 5/0004; A61B 5/259; A61B 5/262; A61B 5/29; A61B 2562/125; A61B 2562/164
See application file for complete search history.

(56) References Cited

U.S. PATENT DOCUMENTS

2011/0295100 A1* 12/2011 Hegde .................... A61B 5/262 600/372
2014/0324113 A1* 10/2014 Savage ................ A61N 1/0492 607/8

(Continued)

OTHER PUBLICATIONS

"Skin preparation-free, stretchable microneedle adhesive patches for reliable electrophysiological sensing and exoskeleton robot control"; Heesoo Kim et al; Science Advances | Research Article; Science Advances (ISSN 2375-2548) is published by the American Association for the Advancement of Science. 1200 New York Avenue NW, Washington, DC 20005.

*Primary Examiner* — Eun Hwa Kim
(74) *Attorney, Agent, or Firm* — S. J. Intellectual Property Limited

(57) ABSTRACT

Disclosed are a stretchable microneedle adhesive patch (SNAP) capable of performing high-quality electrophysiological (EP) signal measurement without skin preparation, such as exfoliating the skin or removing sweat, a SNAP system, and an operating method thereof. The disclosed SNAP capable of performing skin preparation-free high-quality EP signal measurement includes an electrically conductive adhesive (ECA) layer configured to attach to a user's skin to obtain an EP signal regardless of the user's skin condition; a microneedle sensor including a microneedle array configured to penetrate the stratum corneum by passing through the ECA layer and to directly contact the skin epidermis of the user; and conductive wire-based stretchable interconnects having a serpentine structure that is electrically and mechanically connected to the microneedle sensor to dynamically adapt to skin deformation of the user.

18 Claims, 32 Drawing Sheets

(51) Int. Cl.

| | |
|---|---|
| ***A61B 5/262*** | (2021.01) |
| ***A61B 5/296*** | (2021.01) |
| *A61H 1/02* | (2006.01) |
| *A61H 3/00* | (2006.01) |

(52) U.S. Cl.

CPC ... *A61B 2562/125* (2013.01); *A61B 2562/164* (2013.01); *A61H 1/0255* (2013.01); *A61H 3/00* (2013.01); *A61H 2003/007* (2013.01); *A61H 2201/1246* (2013.01); *A61H 2201/1626* (2013.01); *A61H 2201/164* (2013.01); *A61H 2201/165* (2013.01); *A61H 2201/1659* (2013.01); *A61H 2230/605* (2013.01)

(56) References Cited

U.S. PATENT DOCUMENTS

2019/0159337 A1* 5/2019 Wang .................... H05K 1/028
2025/0177737 A1* 6/2025 Choi ........................ A61N 1/37

* cited by examiner

SKIN-PREPARATION-FREE, STRETCHABLE MICRONEEDLE ADHESIVE PATCHES FOR HIGHLY RELIABLE ELECTROPHYSIOLOGICAL MONITORING

CROSS-REFERENCE TO RELATED APPLICATION(S)

This application claims the priority benefit of Korean Patent Application No. 10-2024-0028054, filed on Feb. 27, 2024, in the Korean Intellectual Property Office, the disclosure of which is incorporated herein by reference.

BACKGROUND

1. Field of the Invention

Example embodiments relate to a stretchable and adhesive microneedle electrode capable of performing high-quality electrophysiological (EP) signal measurement without skin preparation and an operating method thereof.

2. Description of the Related Art

As the elderly population increases, the demand for digital healthcare that may accurately monitor a user's physical health and provide appropriate feedback is also increasing. Therefore, a soft wearable sensor is required that has a simple preparation process for wearing, provides long-term comfortable wearability, and performs high-quality electrophysiological (EP) signal measurement.

The development of a high-quality EP signal sensor device is expected to be applicable to various healthcare applications including medical diagnosis, human-machine interface, and rehabilitation engineering, and to be useful in various industrial fields.

A wearable EP signal sensor is used for various purposes (e.g., electrocardiogra electromyography, electroencephalography, etc.) and is an essential element in human-machine interface, digital healthcare, and medical diagnosis. As for the existing wearable EP signal sensor, inexpensive wet electrodes that can obtain a signal of appropriate quality are mainly used. However, due to issues, such as degradation in signal quality by evaporation of moisture in gel during long-term use, various types of dry electrodes have been developed recently.

To be used on the skin for a long period of time without any discomfort, a sensor needs to maintain a low modulus similar to the skin tissue, appropriate adhesin, and breathability. Also, to measure a high-quality electrophysiological signal with a high signal-to-noise ratio, the sensor needs to have low skin contact impedance.

The existing widely used wet/dry clinical electrode has the probability of degrading signal quality according to a decrease in the gel moisture and causing an allergic reaction on the skin and is unsuitable for long-term monitoring accordingly.

A recently developed thin-film epidermal electronics refer to a dry electrode that maintains conformal contact along the curves of the skin and greatly improved long-term wearability. However, this electrode has significant difference in signal quality depending on the skin condition (e.g., hair, dead skin cell, sweat) and is often attached to the skin by van der Waals force without self-adhesiveness, making signal acquisition difficult during intense exercise or sweating.

To overcome such shortcomings, a flexible microneedle electrode is developed that improves signal quality by penetrating the stratum corneum of the skin and by directly contacting the epidermal layer. However, due to a large difference in a modulus between an electrode substrate and skin tissue and the lack of appropriate elasticity and adhesiveness, it is not suitable for comfortable long-term wearing.

SUMMARY

A technical subject to be achieved by the present invention is to provide a microneedle array sensor with excellent stretchability, adhesiveness, and electrical conductivity that may measure a high-quality electrophysiological (EP) signal over a long term without the skin preparation, such as pre-exfoliation of skin and removal of sweat, and an operating method thereof. According to example embodiments, a stretchable and adhesive wearable microneedle sensor patch makes it possible to measure a high-quality biosignal stably for a long period of time regardless of the skin condition and movement of a user.

According to an aspect, a stretchable microneedle adhesive patch (SNAP) capable of performing high-quality EP signal measurement without skin preparation, such as exfoliating the skin or removing sweat, includes an electrically conductive adhesive (ECA) layer configured to attach to a user's skin to obtain an EP signal regardless of the user's skin condition; a microneedle sensor including a microneedle array configured to penetrate the stratum corneum by passing through the ECA layer and to directly contact the skin epidermis of the user; and conductive wire-based stretchable interconnects having a serpentine structure that is electrically and mechanically connected to the microneedle sensor to dynamically adapt to skin deformation of the user.

The ECA layer may be configured to enhance an electrical interface between the microneedle sensor and the user skin by providing an additional electrical conductive path to the user's skin around the microneedle sensor and by lowering skin contact impedance between the microneedle sensor and the user's skin.

The ECA layer may be configured to simultaneously provide electrical conductivity and skin adhesion through silicone-based electrically conductive adhesives coating the conductive wire serpentine interconnects and the microneedle sensor and to implement low impedance between the microneedle sensor and the user's skin.

The microneedle sensor may be configured to integrate a gold-coated silicon microneedle array under the stretchable serpentine interconnects, and to allow the gold-coated silicon microneedle array to penetrate into the stratum corneum of the user and to directly contact the skin stratum corneum without reaching a pain receptor.

The microneedle sensor may be configured to form a microneedle array through partial dicing and isotropic wet etching of a silicon (Si) wafer, followed by deposition of titanium (Ti) and gold (Au), and individually isolated microneedles may be generated through wet etching while coating electrically conductive adhesives on the front of a gold-coated silicon microneedle array and then protecting a lower portion of the microneedle array with the deposited gold and wax applied to sides of the microneedle, and the isolated microneedle array may be generated through integration with the electrically and mechanically connected serpentine stretchable conductive-wire-based using conductive epoxy.

The conductive wire-based stretchable interconnects may be in a form in which conductive wires are integrated on a stretchable substrate, and are configured to transfer obtained EP signals to a circuit unit for analysis of the EP signals through electrical connection to the microneedle sensor.

The conductive wire-based stretchable interconnects may be in a form in which conductive wires are integrated on a stretchable substrate, and may be configured to dynamically accommodate deformation of the user's skin through a serpentine structure and to provide elasticity and comfortable long-term wearability.

The SNAP may be configured to provide adhesion through the microneedle sensor and the ECA layer having a modulus similar to that of the user's skin tissue and to provide elasticity through the conductive wire-based stretchable interconnects, preventing detachment of the SNAP, and to reduce stress on the user's skin tissue to prevent skin rash and irritation and to perform EP signal measurement without quality degradation even after long-term attachment.

According to another aspect, a SNAP system capable of performing preparation-free high-quality EP signal measurement includes a SNAP configured to attach to a user's skin and to be surrounded by a stretchable substrate that obtains an EP signal; a stretchable electronic circuit configured to electrically connect to the SNAP for analysis of the obtained EP signal, to receive the EP signal, and to be surrounded by the stretchable substrate; a chip component including a Bluetooth low-energy system-on-chip (BLE SoC) and an amplifier configured to perform real-time multichannel EP signal monitoring for the EP signal received by the stretchable electronic circuit using a user interface application program; and a modular lithium polymer (LiPo) battery configured to connect to the stretchable electronic circuit through a metal pin connector and to supply power to the SNAP system.

A metal opening on the bottom of the stretchable electronic circuit may provide an electrical connection to the SNAP system via an anisotropic conductive film cable and a magnetic connector to allow semi-permanent use of a circuit and replacement of the SNAP.

The stretchable substrate may be configured to provide dynamic compliance to bending and stretching during the user's skin tissue deformation in the process of attaching to the user's skin and obtaining the EP signal by surrounding the SNAP and the stretchable electronic circuit of the SNAP system.

The chip component including the BLE SoC and the amplifier may be configured to support closed-loop control of an exoskeleton robot through real-time multichannel EP signal monitoring and communication with a control unit using a user interface application program using Bluetooth-based wireless communication.

According to example embodiments, since a skin preparation process for reducing skin contact impedance of an electrode is not required through a stretchable and adhesive wearable microneedle sensor patch, it is possible to save an amount of time and manpower used to wear a wearable sensor system and to improve productivity accordingly. Also, by minimizing the influence of the skin condition and motion artifacts and by enabling high-quality EP signal measurement, it is possible to make great contribution to human-machine interface application in which high-fidelity EP signal measurement is essential for accurate movement. It may be applied to wearable digital healthcare technology that requires high-quality wearability in terms of stably operating for a long period of time regardless of the skin condition and not causing skin rash or irritation due to its comfortable wearability.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
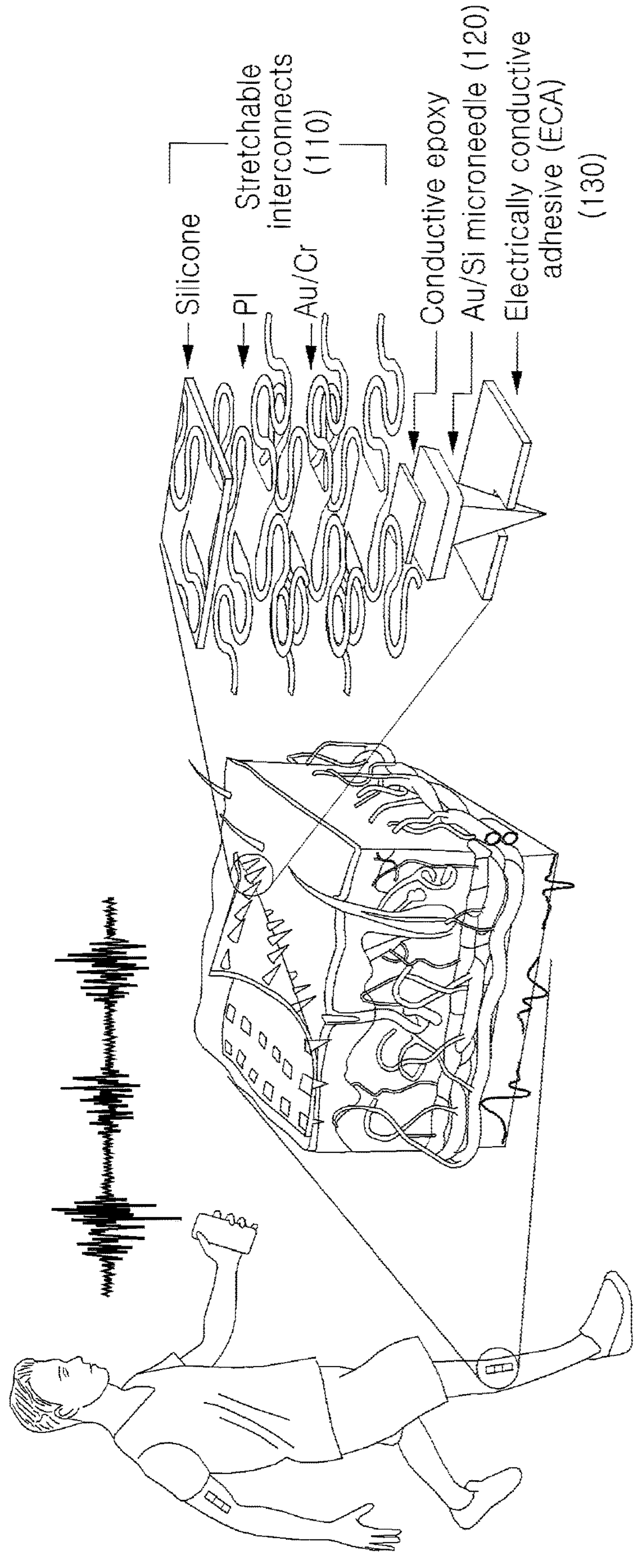
FIG. 1 illustrates a configuration of a stretchable microneedle adhesive patch (SNAP) according to an example embodiment.

High accuracy and convenient recording of electrophysiological (EP) signals is essential for health care and human-machine interface (HMI). A microneedle electrode is directly accessible to the epidermis, allowing immediate setup without a time-consuming skin preparation process. However, the existing microneedle electrode lacks elasticity and reliability required for robust skin interfacing, thereby making long-term, high-quality EP sensing challenging during body movement. Here, proposed is a stretchable microneedle adhesive patch (SNAP) that provides excellent skin penetrability and a robust electromechanical skin interface for prolonged and reliable EP monitoring under variety of the skin condition. According to an example embodiment, results demonstrate that the SNAP may substantially reduce skin contact impedance under skin contamination and enhance wearing comfort during motion, outperforming gel and the flexible microneedle electrode. Wireless SNAP demonstration for exoskeleton robot control shows its potential for highly reliable HMI, even under time-dynamic skin conditions. The SNAP according to an example embodiment is expected to provide variety for wearable EP sensing and its real-world applications in HMIs.

Reliable and accurate recording of electrophysiological (EP) signals from the skin is crucial for clinical diagnosis, rehabilitation, and HMI. A preparation-free EP sensor with superior recording quality over extended period regardless of the skin condition may bring practical impact on a wide variety of real-world wearable applications. Conventionally, clinical metal electrodes with conductive gel or electrodes with hydrogel are commonly used for EP sensing due to their satisfactory signal acquisition performance and cost-effectiveness. However, these electrodes require cumbersome preparation steps, such as applying gel and cleaning the skin with alcohol swabs, and experience signal degradation due to the drying of gel over time. Also, their interface susceptible to sliding with gel may cause motion artifacts. In addition, the conductive gel may potentially induce skin allergies or irritations, inhibiting prolonged use of the electrodes.

Advancement in materials and microfabrication techniques has attempted to overcome such limitation by developing soft and dry epidermal electrodes that offer comfortable long-term EP signal monitoring without the need for electrolyte gel. Nevertheless, without skin preparation, such as cleaning and exfoliation, a dry electrode attached to the skin surface typically exhibits high and unstable skin contact impedance due to factors, such as hair, the stratum corneum, and skin secretion. In addition, an epidermal electrode maintaining contact with the skin solely through van der Waals force may cause an unstable electrode-skin interface during sweating and strenuous movement. In some cases of tattoo-like electrodes, device preparation needs additional equipment, such as a stencil mask or a spray printer, to print on the skin, hindering the ease of use.

A solution to mitigate the vulnerability of an EP sensor to the skin condition may be a microneedle electrode. The microneedle electrode provides a stable electrical interface without a skin preparation process, facilitated by epidermis accessibility enabled through penetration of the microneedle. In the art, flexible microneedle electrodes (FMEs) built on polymer substrates, such as polyimide (PI), polystyrene, and parylene, are demonstrated. Although the FMEs are materially biocompatible, their high modulus of the substrate, which does not mechanically match with the skin tissue, leads to interface failure issues and discomforting during long-term wearing. Recent development of stretchable microneedle electrode using a polydimethylsiloxane (PDMS) substrate partially alleviated a modulus mismatch issue. However, such electrodes still encounter challenge in conforming to tissue strain due to their higher modulus than the tissue and lack of adhesion to the tissue surface. Furthermore, the EP signal recording performance of the existing stretchable microneedle electrode was barely investigated because of difficulties in making electrical connection and insufficient reliability during mechanical elongation.

The present invention presents a stretchable microneedle adhesive patch (SNAP) as a solution for preparation-free, highly reliable, and long-term EP signal monitoring irrespective of the skin condition. A stretchable platform of the SNAP includes serpentine interconnects and accommodates the dynamic change of the skin tissue and improves wearing comfort over a long period. Incorporating silicon (Si) microneedle arrays beneath the stretchable interconnects enables their penetration into the stratum corneum, providing direct contact with the epidermis without reaching the pain receptors. This facilitates high-quality EP signal acquisition free from pain and the skin preparation process. Also, electrically conductive adhesive (ECA) including silver (Ag) flakes and high-tack silicone not only enhances an electrode-skin interface by providing an additional conductive path, but also ensures secure adhesion to the skin during usage. Through a series of studies, physical, mechanical, and electrical characteristics of the SNAP are comprehensively investigated, confirming their potential for highly reliable long-term EP signal monitoring in various situations. Finite element analysis (FEA) results and experimental comparison with other types of EP sensors (e.g., FMEs and gel electrodes) demonstrate that the SNAP substantially reduces tissue stress during skin deformation and enhances a signal-to-noise ratio (SNR) due to their elastic and penetrable nature. Proof-of-concept demonstration in a closed-loop operation of an exoskeleton robot highlights the reliability of a skin preparation-free wireless SNAP system, showcasing its potential for HMI application allowing quick, seamless setup and freedom of movement for a user. Herein, it is anticipated that the SNAP will bring a broad impact on various application fields requiring reliable EP sensing, such as continuous health monitoring, neurological research, and wearable HMI.

FIG. 1 illustrates a configuration of a stretchable microneedle adhesive patch (SNAP) according to an example embodiment.

A patch-type device integrated with the SNAP according to an example embodiment may perform stable long-term EP signal monitoring regardless of the skin condition. FIG. 1 is a close-up view of a soft, tissue-adapting SNAP that uses a microneedle (Au/Si microneedle) to penetrate the stratum corneum for direct access to the epidermis.

The SNAP according to an example embodiment is engineered to have softness, adhesive property, and tissue adaptability, ensuring long-term and reliable EP signal recording.

Referring to FIG. 1, the SNAP according to an example embodiment includes a conductive wire-based stretchable interconnects (stretchable interconnects) 110, a microneedle sensor (Au/Si microneedle) 120 including an Au-coated Si microneedle array, and an electrically conductive adhesive (ECA) 130 made of Ag flakes and Silicone polymer. The silver flakes may be replaced with other electrical conductive filters, such as carbon nanotube, graphene, carbon black, silver nanowire, and liquid metal.

The SNAP according to an example embodiment may perform stable high-quality biosignal measurement over a long period of time regardless of the user's skin condition and movement.

The conductive wire-based stretchable interconnects (i.e., stretchable substrate) 110 according to an example embodiment are designed in a serpentine shape (e.g., 5 μm/200 nm/5 μm PI/Au/PI structure) and serve as electrical and mechanical foundation for the microneedle array.

This serpentine design renders the overall SNAP elastic, allowing the SNAP to dynamically adapt to skin deformation. The rigid Si microneedle (e.g., elastic modulus of 130 GPa) 120 integrated underneath the serpentine stretchable interconnects 110 allows easy insertion through the stratum corneum to reach the epidermis. This architecture lowers contact impedance, enhancing the electrode performance. The microneedle according to an example embodiment is designed to have a height of 200 μm and a tip diameter of less than 5 μm and ensures pain-free insertion into the skin since a pain receptor is present below 200 μm from the skin surface.

The ECA (e.g., 45 μm in thickness) 130 surrounding the microneedle according to an example embodiment provides an additional electrical conductive path from the skin, thereby enhancing an electrical interface between the electrode and the skin. The ECA 130 according to an example embodiment includes high-tack silicone-Ag composite, and offering strong adhesion to skin. The silver flakes may be replaced with other electrical conductive filters, such as carbon nanotube, graphene, carbon black, silver nanowire, and liquid metal.

Figure 2A:
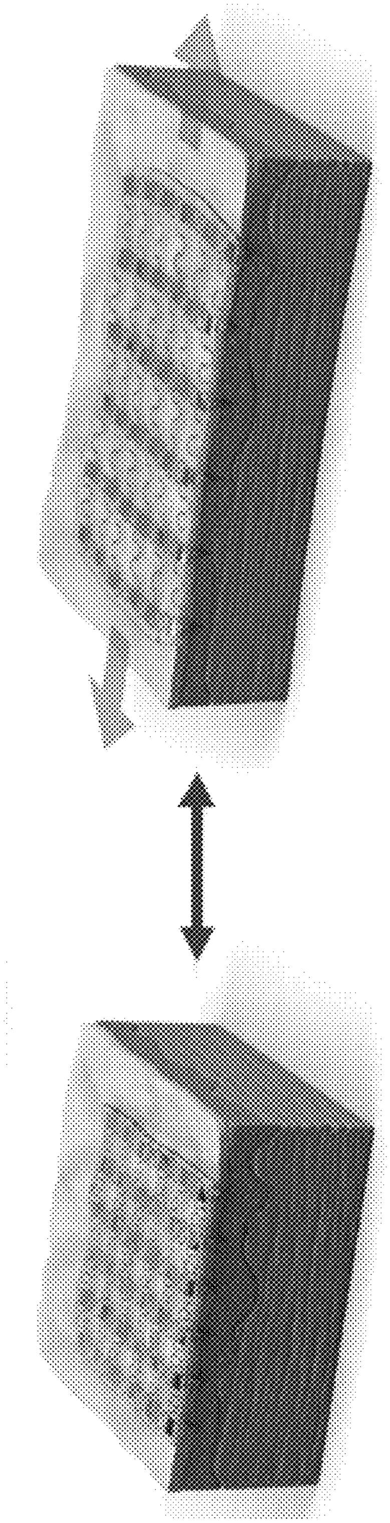
FIGS. 2A, 2B, and 2C illustrate major mechanical feature of a SNAP for reliable wearable EP signal monitoring according to an example embodiment.
Figure 2B:
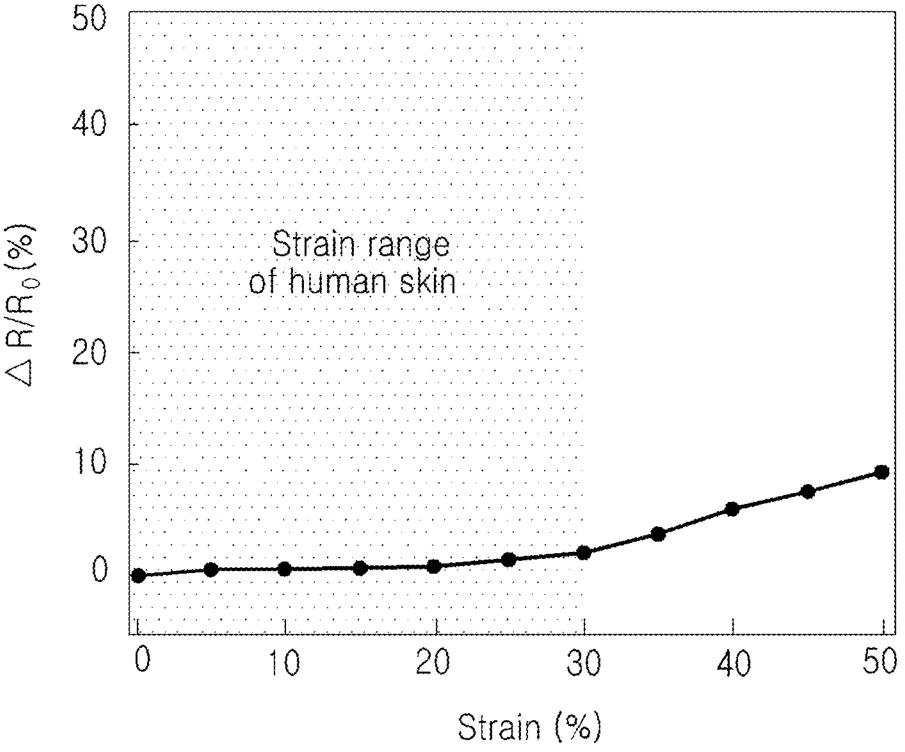
Figure 2C:
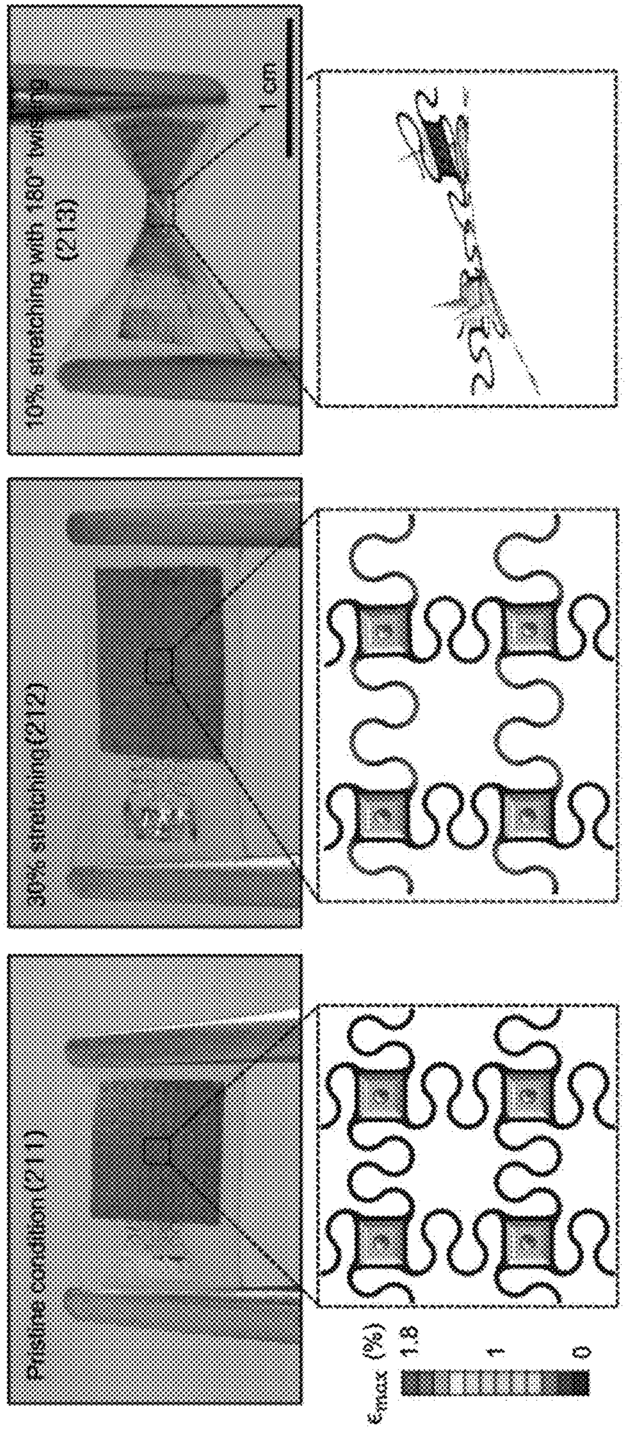

FIGS. 2A, 2B, and 2C illustrate major mechanical feature of a SNAP for reliable wearable EP signal monitoring according to an example embodiment.

FIG. 2A illustrates the feature of the SNAP for adapting stretching of the skin tissue.

Referring to FIG. 2A, the soft and stretchable nature of the SNAP establishes a robust interface between a microneedle and the skin, accommodating the dynamic skin deformation with minimal mechanical stress to the skin.

FIG. 2B is a graph showing a relative resistance change of the SNAP as a function of tensile strain. The SNAP according to an example embodiment exhibits a negligible resistance change when subjected to 30% stretching corresponding to the maximum stretching range of the human skin. This highlights its ability to maintain stable electrical measurement under tensile deformation.

FIG. 2C illustrates optical images showing high mechanical compliance of the SNAP, pristine condition 211, 30% stretching condition 212, and 10% stretching condition with 180° twisting 213, and finite element modeling of the SNAP for deformation configuration of each condition.

Experimental and FEA simulation results (see FIG. 2) according to an example embodiment indicate that the SNAP may stretch over the maximum tensile strain range of human skin (about 30%) with negligible relative resistance change (<5%; FIG. 2B) and with only 1.8% maximum principal strain in metal traces. Referring to FIG. 2C (212), yield strain of Au is about 2%. In particular, the majority of the trace region experiences substantially lower strain (<0.5%) compared to the maximum strain. Also, it may withstand extreme deformation (e.g., 180° twisting and 10% stretching) with high mechanical endurance and the maximum principal strain in the metal traces is only 0.097% (see FIG. 2C (213)). Such results confirm the excellent electrical and mechanical reliability of the SNAP at a strain level beyond typical tolerance of human skin (10 to 20%). Overall, a design that integrates the microneedle array with the tissue-conformal elastic electrode may provide comfortable and highly reliable EP signal monitoring, with minimal interference from various skin conditions.

Figure 3:
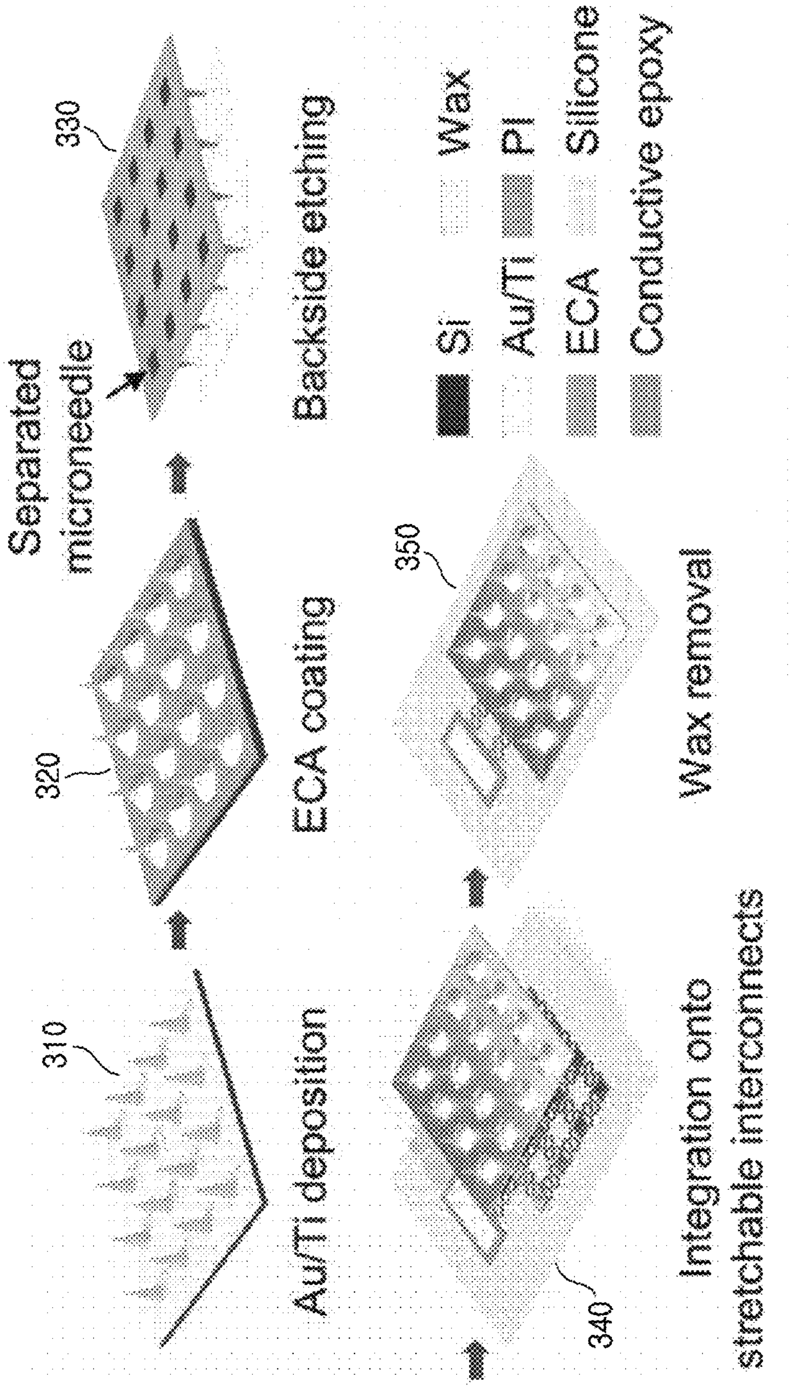
FIG. 3 illustrates a fabrication process and material of a SNAP according to an example embodiment.

FIG. 3 illustrates a fabrication process and material of a SNAP according to an example embodiment.

The fabrication process of FIG. 3 shows a fabrication step for integrating a rigid microneedle array onto an elastic electrode. Initially, the microneedle array is formed by partial dicing and isotropic wet etching of a Si wafer, followed by titanium (Ti)/gold (Au) (20/200 nm) deposition (310). Then, an uncured, low-viscous ECA is poured over the frontside of the Au-coated Si microneedle array (320). Subsequently, individually isolated microneedles are generated by wet etching the bottom of the Si microneedle array of the Si microneedle array, while protecting the ECA layer by the deposited Au layer and wax applied on the microneedle side (330). The isolated microneedle array is electrically and mechanically integrated with serpentine interconnects using conductive epoxy (340), and the fabrication process is completed by removing the wax (350).

FIGS. 4A to 4H illustrate a configuration and mechanical feature of a stretchable and adhesive microneedle sensor according to an example embodiment.

The conductive wire-based stretchable interconnects (i.e., stretchable substrate) according to an example embodiment are in a form in which conductive wires are integrated into a low modulus silicone elastomer, and are freely adaptable to dynamic deformation of the skin, and electrically connected to a microneedle array to transmit an EP signal to a circuit unit. Here, the low modulus silicone elastomer is only an example and, in addition thereto, various stretchable substrates may be used.

A microneedle sensor including the Au-coated Si microneedle array according to an example embodiment is electrically and mechanically connected to the stretchable interconnects to penetrate the highly resistive stratum corneum of the skin and directly contact the stratum corneum, thereby effectively reducing skin contact impedance. Silver flake-silicone polymer-based electrical conductive adhesives coating the stretchable interconnects and the microneedle array implement robust electrode-skin impedance by simultaneously having high electrical conductivity and adhesion to the skin.

Figure 4A:
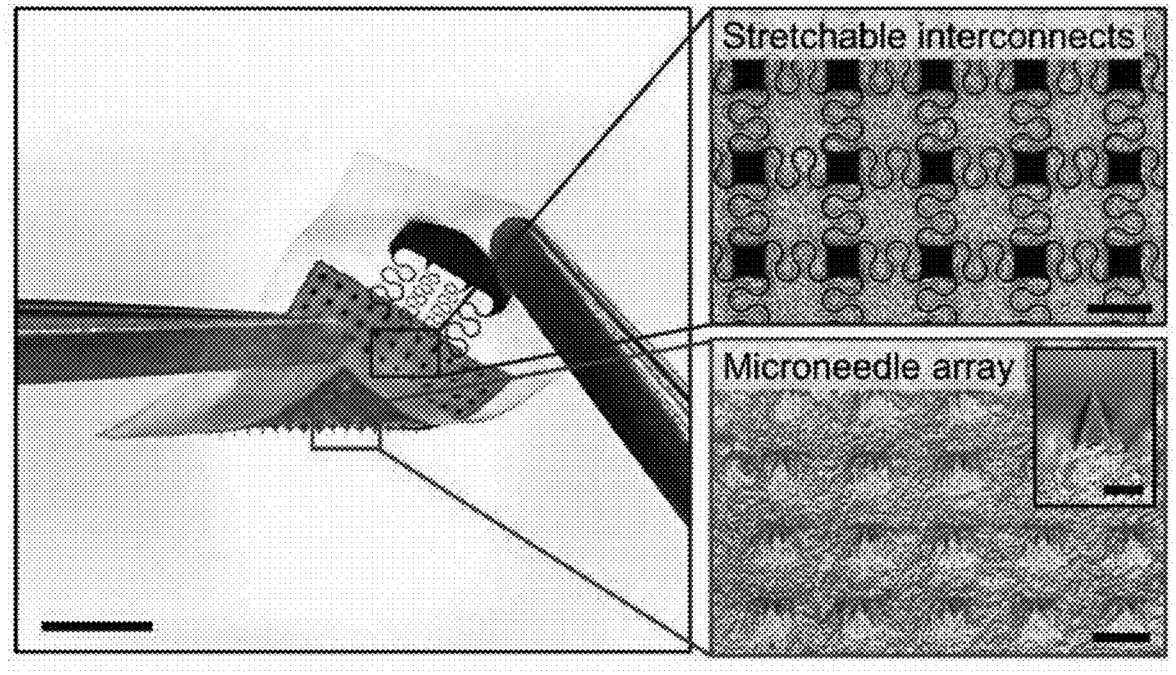
FIGS. 4A to 4H illustrate a configuration and mechanical feature of a stretchable, adhesive microneedle sensor according to an example embodiment.

FIG. 4A illustrates an optical image of a completed stretchable, adhesive microneedle sensor (scale bar, 5 mm). Images on the right show the completed SNAP including stretchable interconnects (top image; backside of the device) and an ECA layer-coated microneedle array (bottom image; frontside of the device). Crucial factors for achieving high-quality skin signal recording are excellent epidermis accessibility and robust electrical and mechanical interface with the skin.

Figure 4B:
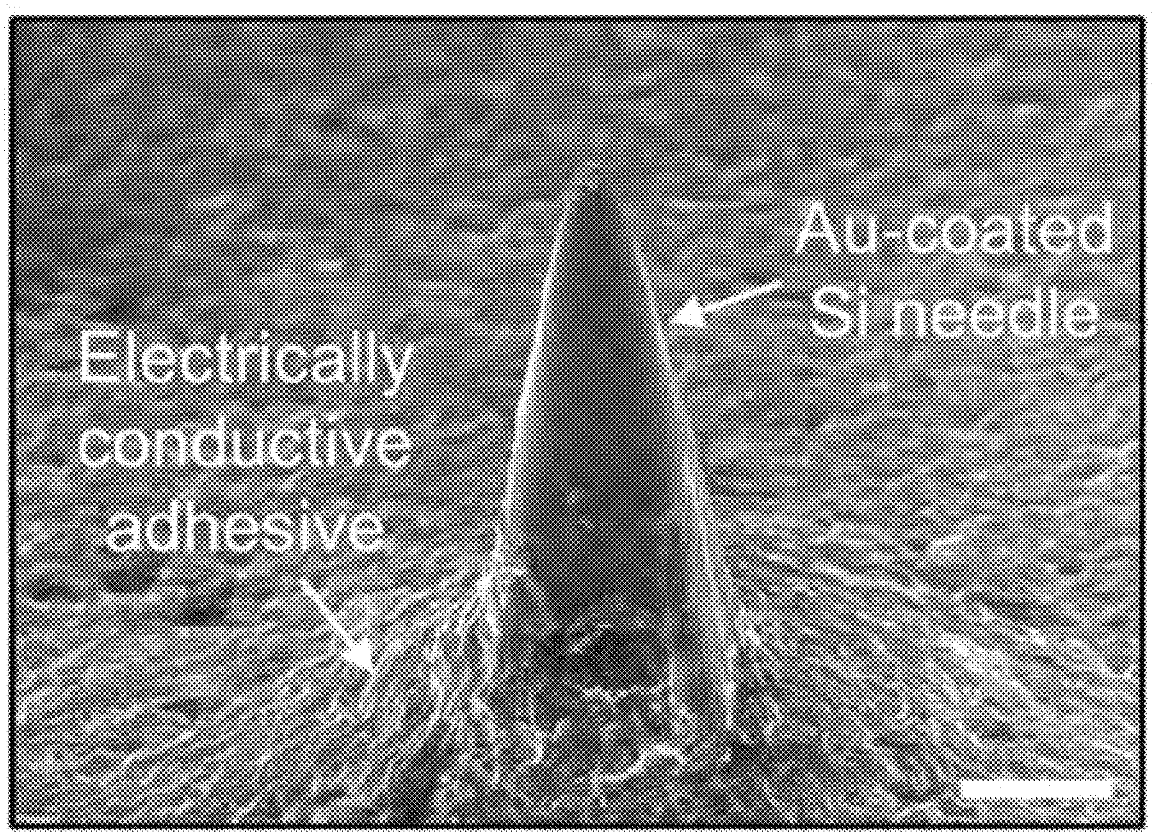

FIG. 4B illustrates a scanning electron micrography (SEM) image of a single microneedle showing an Au-coated tip that protrudes from the ECA layer according to an example embodiment (scale bar, 50 μm).

The SNAP may ensure direct, biocompatible access to the epidermis through a protruding Au-coated microneedle tip, and, at the same time, may maintain strong adhesiveness, high stretchability, and low contact impedance through the ECA layer. This ECA layer is a polymeric composite of surface-modified Ag flakes and high-tack silicone in an optimal ratio (Silbione (5 kPa): Ecoflex GEL (33 kPa)=1:3 (Silbione RT Gel 4717, Bluestar Silicones; Ecoflex GEL, Smooth-On-Inc. (53-55)). Silbione enhances adhesion of ECA and Ecoflex GEL enhances toughness.

Figure 4C:
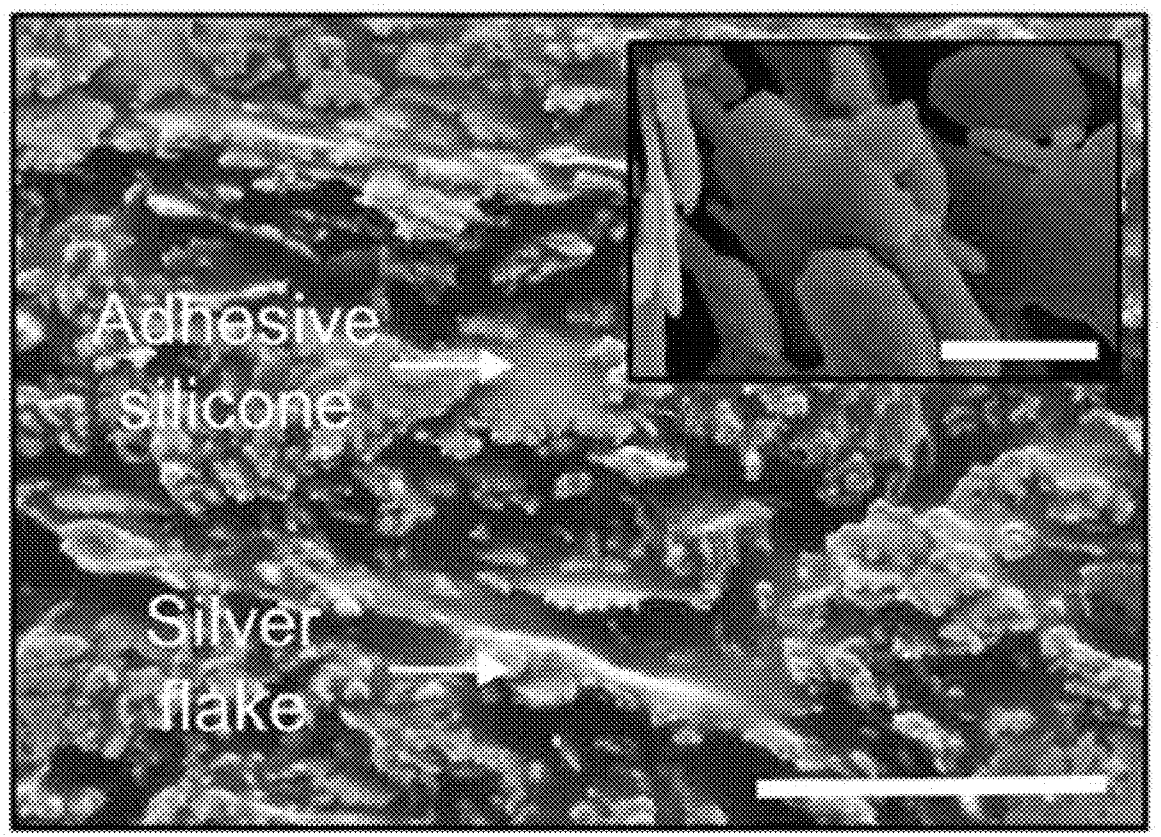

Top of FIG. 4C is a SEM image of an ECA layer showing a mixture of silver (Ag) flakes and silicone gel (Silbione: Ecoflex GEL=1:3) (scale bar, 10 μm). Bottom of FIG. 4C shows Ag flakes with roughened surface according to an example embodiment (scale bar, 1 μm).

The surface-modified Ag flakes play an important role in enhancing the electrical conductivity of ECA. Through an iodination process, the surface of Ag flakes is roughened, leading to formation of Ag/AgI nano-islands that expose silver. This promotes sintering among the Ag flakes, which leads to increasing the intrinsic conductivity of the ECA. Furthermore, the morphology of two-dimensional surface-modified Ag flakes increases the stretching stability of the ECA through parallel-stacking of adjacent flakes along a substrate plane direction during curing of low-viscous conductive polymer. Accordingly, an interparticle distance between adjacent flakes is maintained to some extent within a certain strain range, providing a reliable electrical conductive path less susceptible to stretching. This shows that relative resistance change is small when the ECA is exposed to the allowable maximum tensile strain corresponding to the allowable maximum skin stretching of human skin.

Figure 4D:
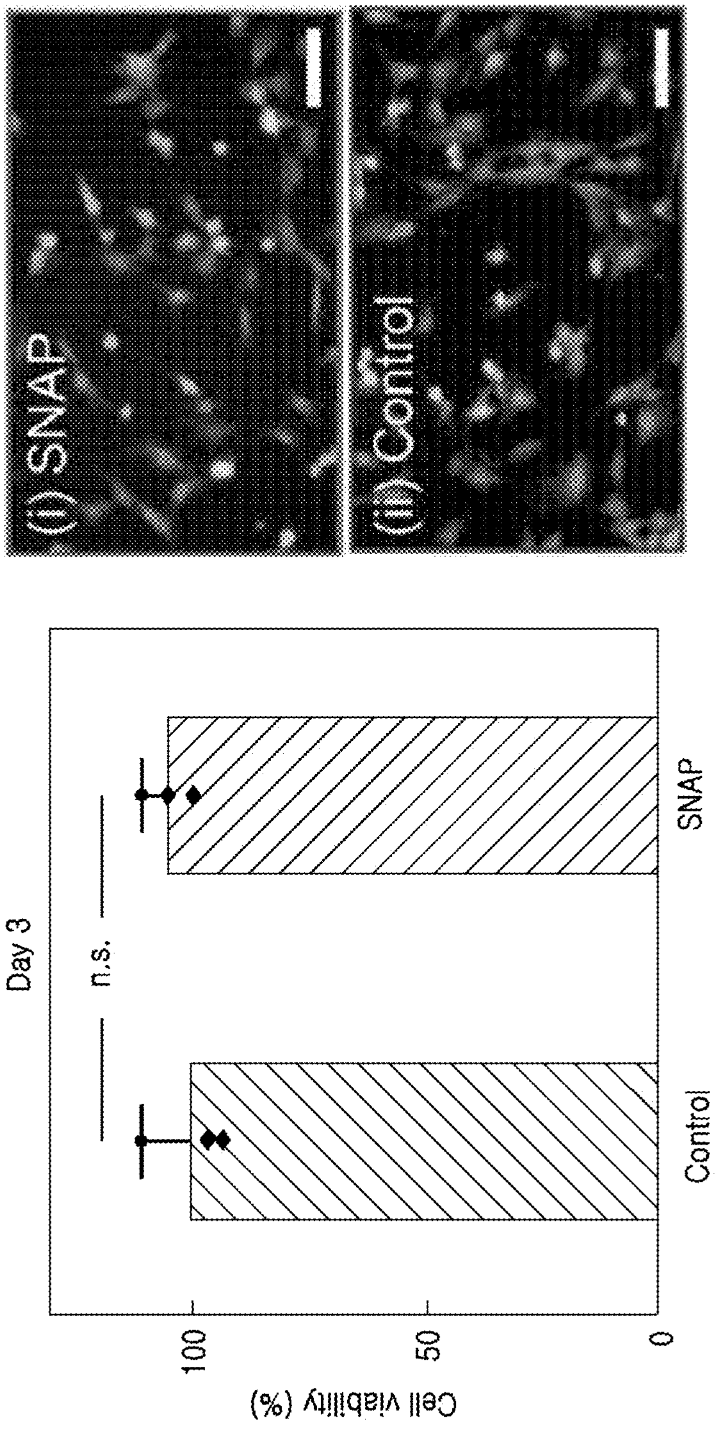

FIG. 4D is a graph comparing cell viability between a control group (without SNAP) and an experimental group (with SNAP immersed) cultured in cell medium on day 3 according to an example embodiment. Images on the right show live/dead staining images of 3T3 cells after a 3-day culture for the SNAP-immersed group (i) and the control group (ii) (scale bar, 100 μm).

Referring to FIG. 4D, experimental results show the on-skin biocompatibility of the SNAP, verifying that the SNAP according to an example embodiment does not cause undesirable harm during long-term use. To assess the biocompatibility of the SNAP, a cytotoxicity test was conducted with 3T3 cells (mice embryonic fibroblast cell line). In this test, the SNAP was fully immersed in the cell medium and incubated with 3T3 cells. The cells cultured in the SNAP-immersed cell medium exhibited comparable cell viability to the control group with complete cell medium on days 3 and 7. Fluorescent live/dead staining clearly demonstrates no notable difference between the control group and the SNAP-immersed group, indicating excellent biocompatibility of the SNAP. Aside from the device biocompatibility, another important aspect to consider is securing sufficient breathability, ensuring comfortable and skin irritation-free wearability while maintaining performance of stable EP signal measurement. On the basis of the permeability test conducted according to ASTM E96-95 standards, the SNAP exhibits excellent water vapor permeability, which falls within the range of trans-epidermal water loss observed in human skin (5 to 10 g hour-1 m-2), verifying the on-skin breathability of the SNAP.

Figure 4E:
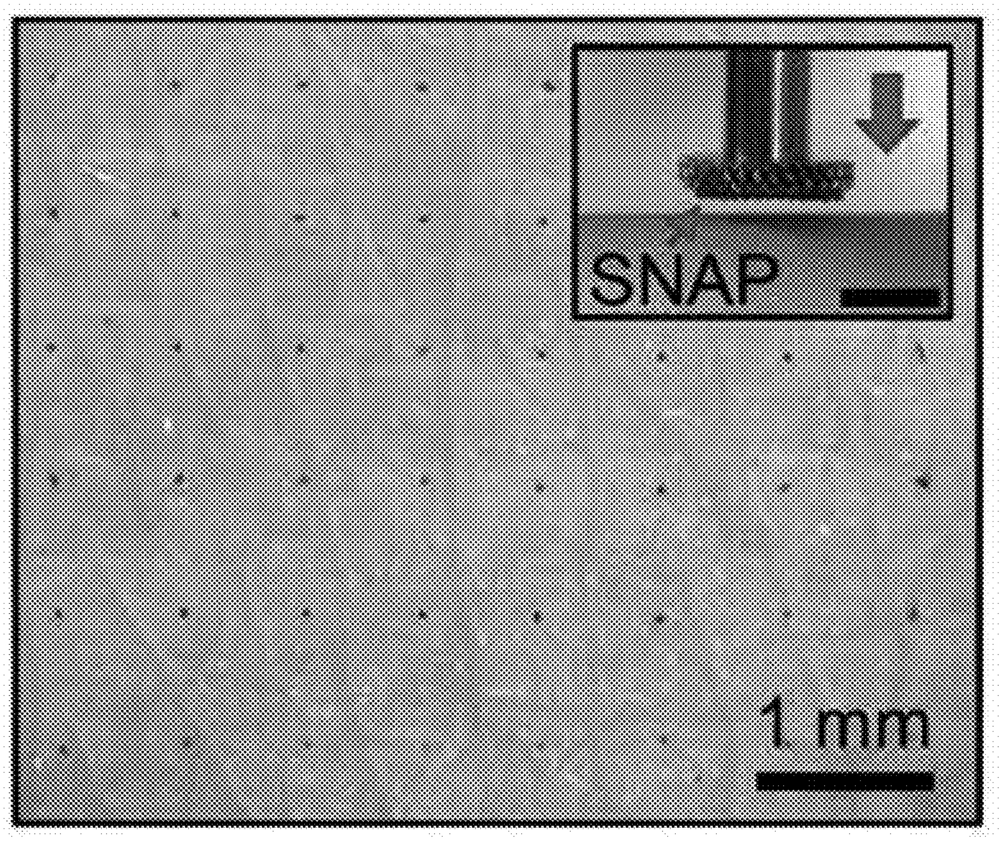

FIG. 4E illustrates an optical image of the human skin stained with blue dye coated on a microneedle array according to an example embodiment. FIG. 4E illustrates experimental setup for skin penetration through the SNAP (scale bar, 1 cm).

One of the key design requirements of the SNAP according to an example embodiment is to achieve uniform skin penetration with low penetration force despite its soft substrate.

Figure 4F:
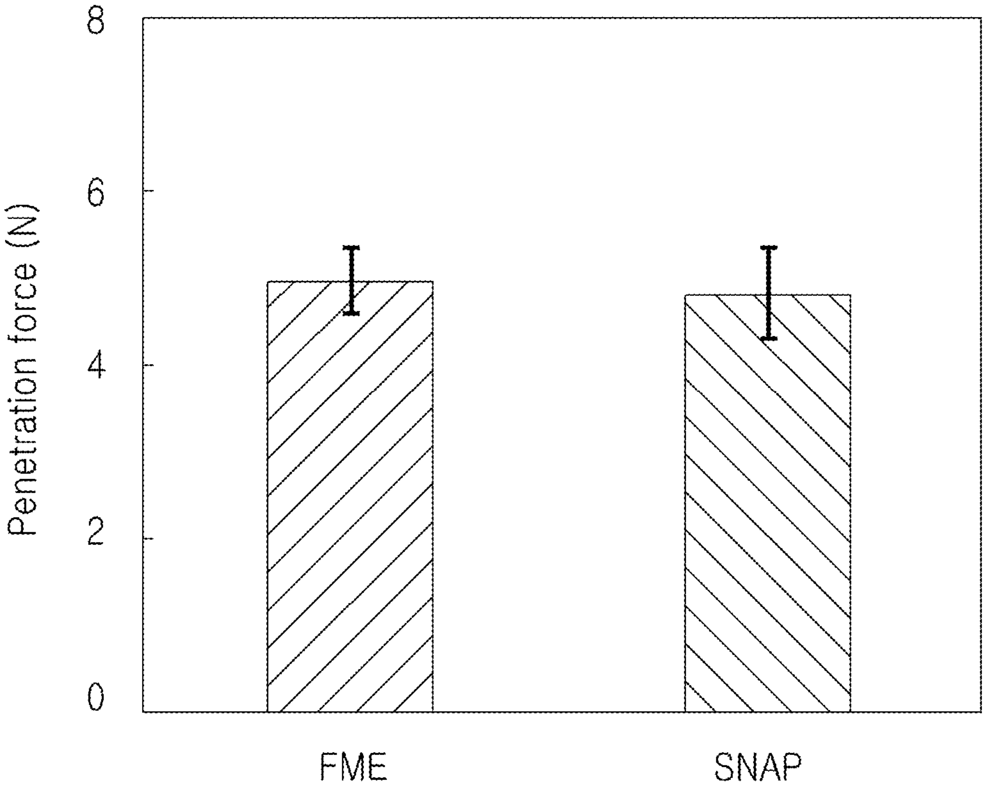

FIG. 4F is a graph comparing skin penetration force between FME and the SNAP according to an example embodiment.

Referring to FIG. 4F, the SNAP exhibits the capability of penetrating the human skin with an insertion force comparable to that of the conventional FME built on PI substrate. The insertion force obtained for the SNAP (≈4.8 N) is clearly lower than the force required to press an elevator button or attach a postage stamp (≈20 N). In addition, as a loading speed increases, the required insertion force decreases. Such results suggest that the SNAP may be easily attached to the skin for robust skin penetration with minimal force, which is achievable even with a gentle finger pressure alone.

Figure 4G:
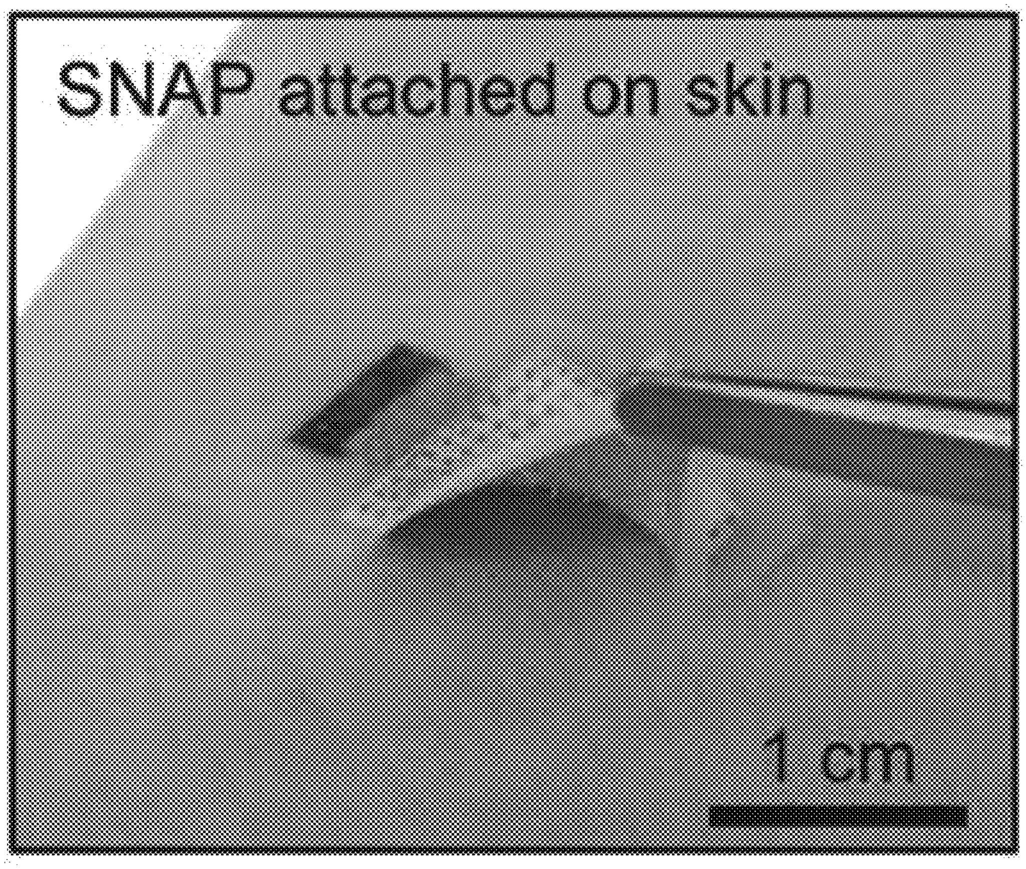

FIG. 4G is an optical image of the SNAP mounted on the skin according to an example embodiment, which shows intentionally partially detached using a tweezer, demonstrating robust adhesion of the device to the skin.

Figure 4H:
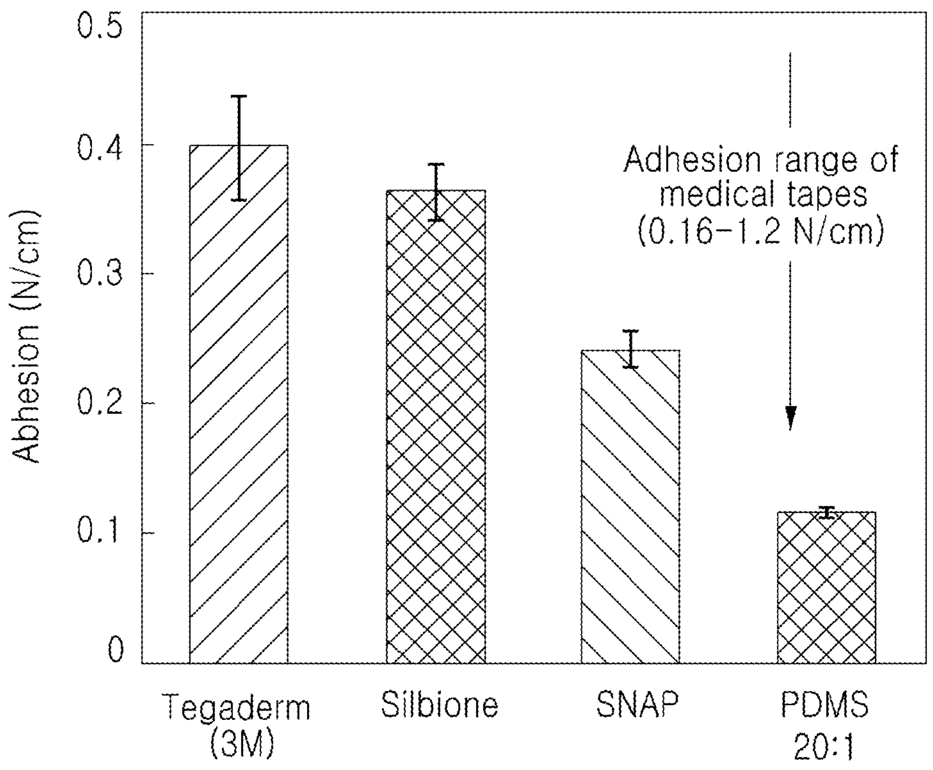

FIG. 4H is a graph showing adhesion strength of the SNAP to the skin compared to that of commercial medical film and silicone adhesives (e.g., Silbione, 20:1 PDMS) according to an example embodiment.

The SNAP according to an example embodiment provides a robust adhesion through the tacky ECA layer after quick attachment and ensures a reliable device interface (0.24 N/cm), which falls within the typical adhesion range of commercial medical adhesive tapes (0.16 to 1.2 N/cm). Overall, biocompatibility, breathability, and mechanical characteristics of the SNAP represent that the SNAP may provide a comfortable and skin-friendly interface to the user while maintaining an excellent device-skin contact.

Figure 5:
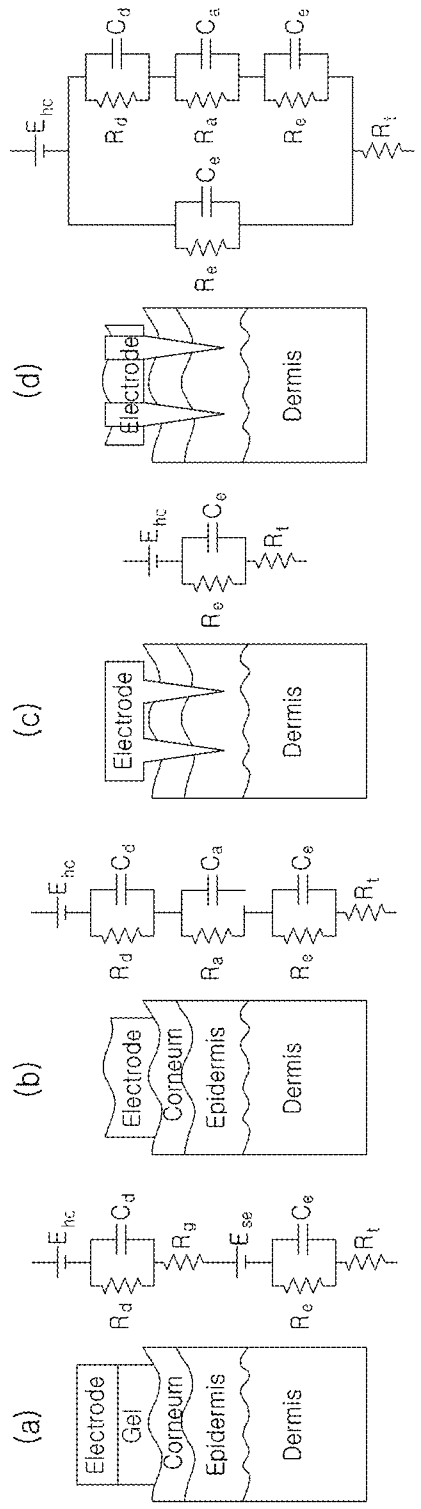
FIG. 5, (a), (b), (c), and (d), are equivalent circuits for describing electrical characteristics of a SNAP attached to the skin according to an example embodiment.

FIG. 5, (a), (b), (c), and (d), are equivalent circuits for describing electrical characteristics of a SNAP attached to the skin according to an example embodiment.

FIG. 5 is a schematic view showing an electrode-skin interface for various types of electrodes with a corresponding equivalent circuit model. (a) of FIG. 5 illustrates a gel electrode, (b) of FIG. 5 illustrates an ECA electrode, (c) of FIG. 5 illustrates FME, and (d) of FIG. 5 illustrates the electrode-skin interface of the SNAP and each equivalent circuit.

The FME was produced by sputtering Ti/Au (20/200 nm in thickness) on a PI-based microneedle electrode, but does not include an ECA layer, which differs from the SNAP. Unlike a surface electrode, the microneedle electrode (e.g., FME and SNAP) circumvent the effect of double layer capacitance (Ca) and charge transfer resistance (Ra) at an electrode-tissue interface. This is achieved by directly accessing the epidermis layer through the penetration of highly resistive stratum corneum (>$10^5$ ohms).

FIGS. 6A to 6I illustrate examples of describing electrical characteristics of a SNAP attached to the skin according to an example embodiment.

Figure 6A:
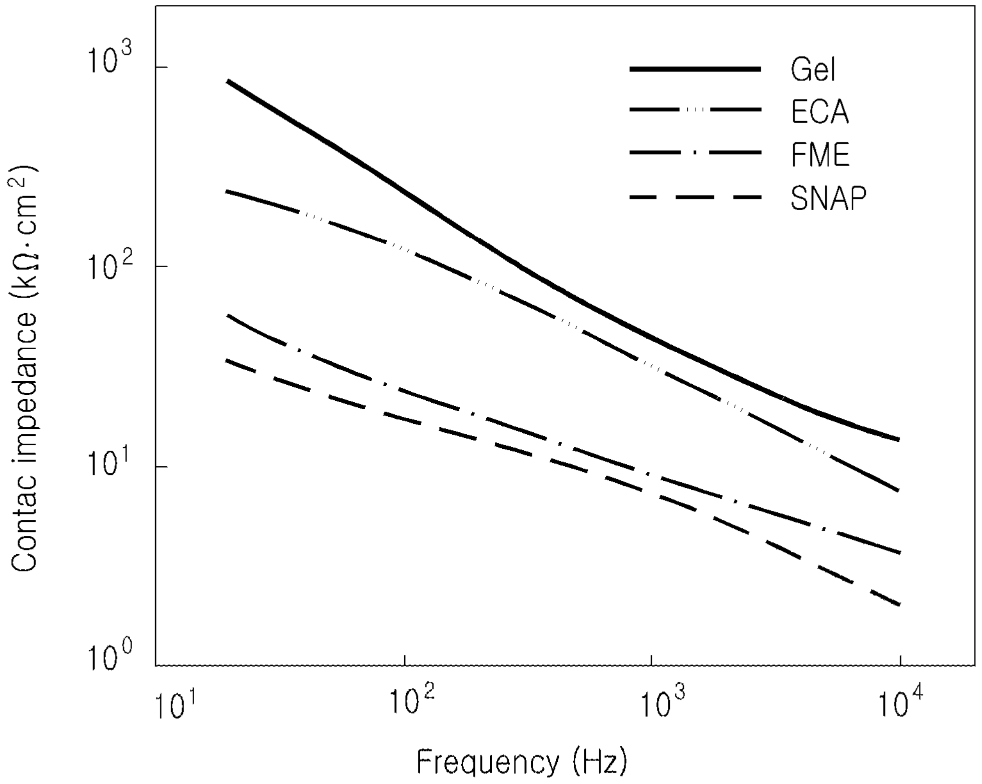
FIGS. 6A to 6I illustrate examples of describing electrical characteristics of a SNAP attached to the skin according to an example embodiment.

Referring to FIG. 6A, a plot of electrode-skin contact impedance changes using a function of frequency. The skin is prepared by wiping the skin with water-soaked gauze for cleaning, followed by another wiping with an alcohol swap for disinfection.

Figure 6B:
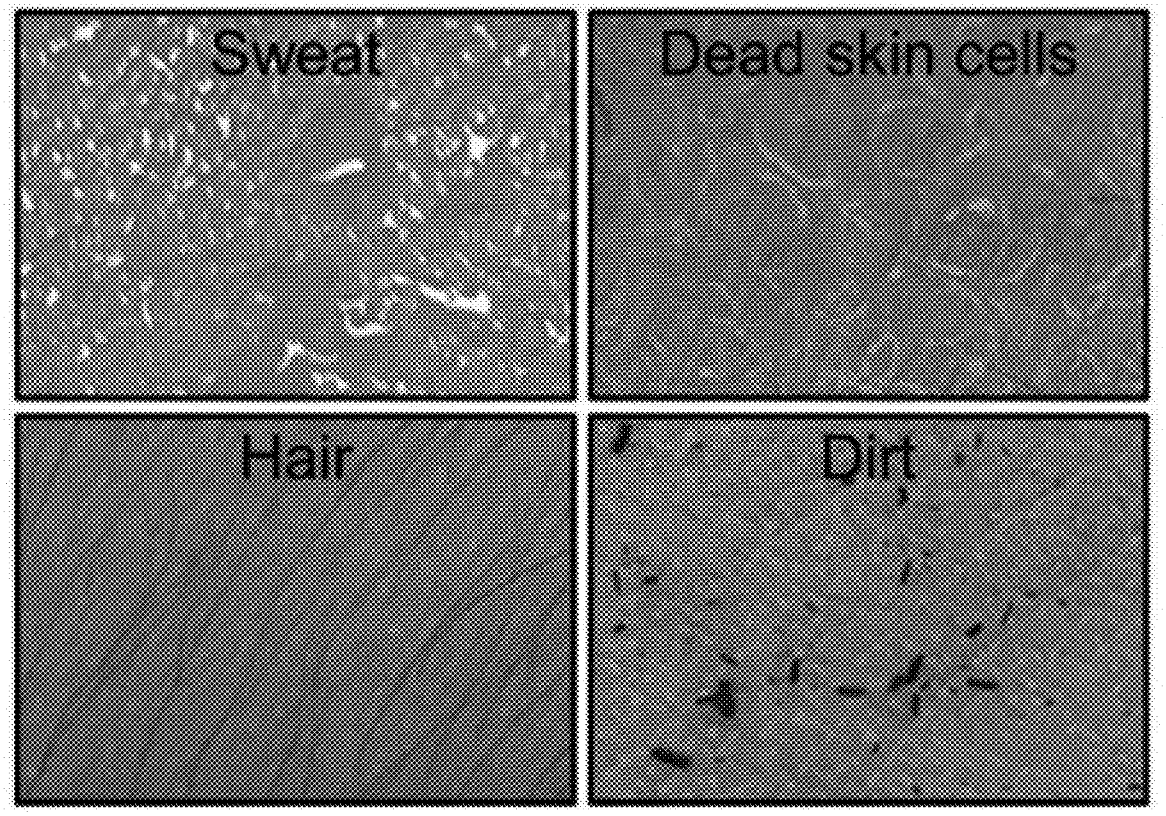
Figure 6C:
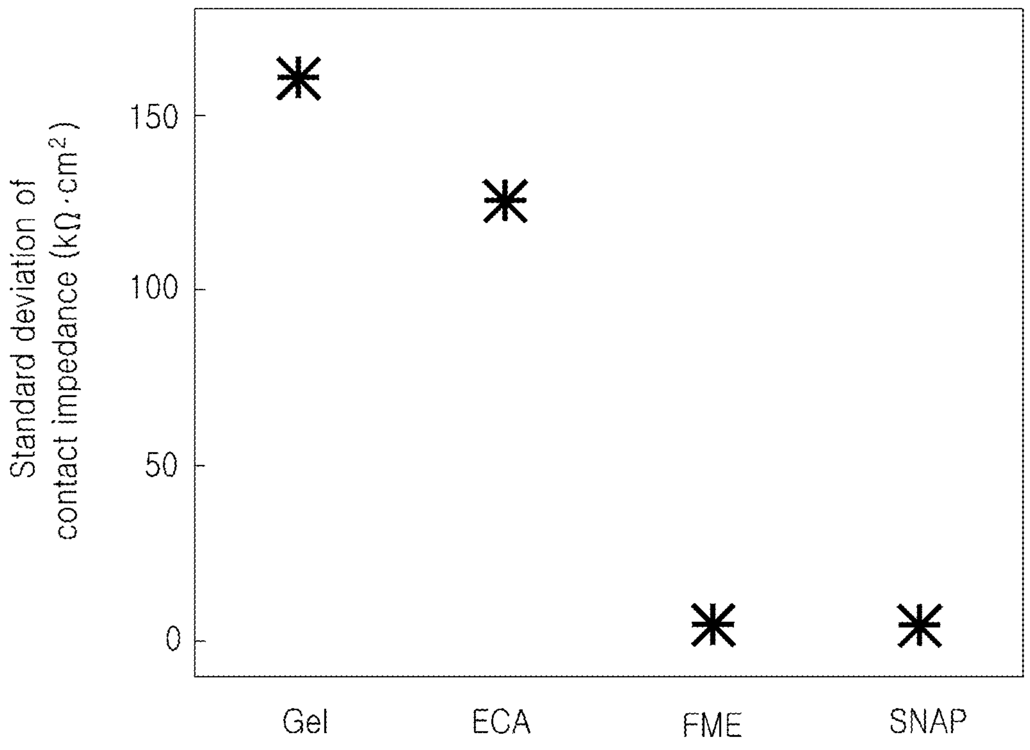

FIG. 6B is optical images showing various skin conditions including the skin with sweat, dead skin cells, hair, and dirt, and FIG. 6C illustrates the standard deviation of skin contact impedance measured with various EP sensors under such various skin conditions.

In the case of the SNAP, the ECA layer surrounding the microneedle array further enhances the electrode-tissue interface by reducing the contact impedance. Specifically, the contact impedance is reduced by 25% at 100 Hz compared to the FME (FIG. 6A). Also, regardless of the skin condition, the SNAP exhibits lower and consistent skin contact impedance (21±5 kohm·$cm^2$ at 100 Hz, mean±standard deviation (SD)), and maintains stable skin contact impedance compared to other electrode types (FIGS. 6A and 6C). In multiple sample trials (n=5), the direct epidermis access provided by the SNAP exhibits the stable and notably lower standard deviation (σ) of skin contact impedance ($\sigma_{SNAP}$ and $\sigma_{FME}$≈5 kohm·$cm^2$), which is lower than the standard deviation of skin contact impedance of conventional gel or ECA electrode ($\sigma_{gel}$ and $\sigma_{ECA}$≈150 kohm·$cm^2$) (FIG. 6C). Through this feature, the SNAP provides excellent electrical performance and does not require skin preparation, such as cleaning or exfoliating.

Figure 6D:
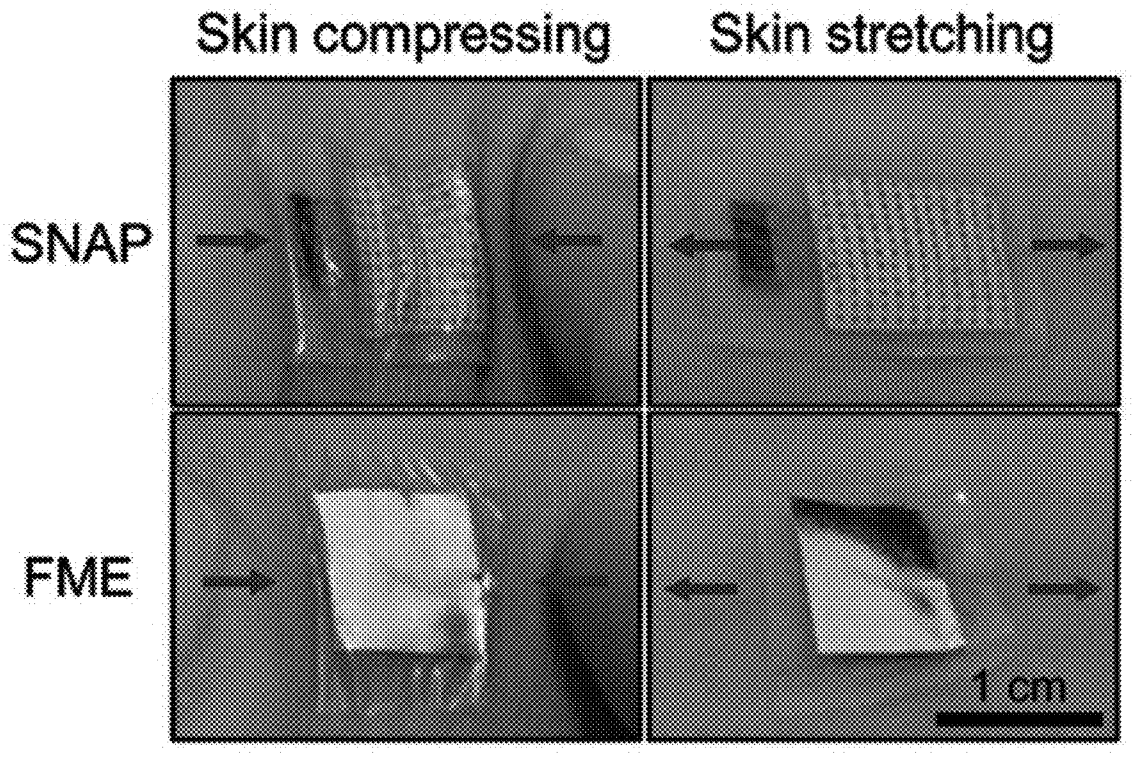

FIG. 6D provides visual comparison of mechanical adaptation between the skin-mounted SNAP and FME during skin compressing and stretching.

The elastic nature of the SNAP allows the SNAP to respond and accommodate dynamic deformation, enabling consistent and stable contact with the skin. In contrast, the FME is easy to delaminate from the skin due to mechanical mismatch at a device-skin interface.

The stretchable, adhesive microneedle electrode according to an example embodiment has a modulus similar to that of the skin tissue (e.g., 60-850 kPa) and excellent elasticity (>50%) and dynamically adapts to stretching of the skin and prevents detachment of the electrode (FIG. 6D).

Figure 6E:
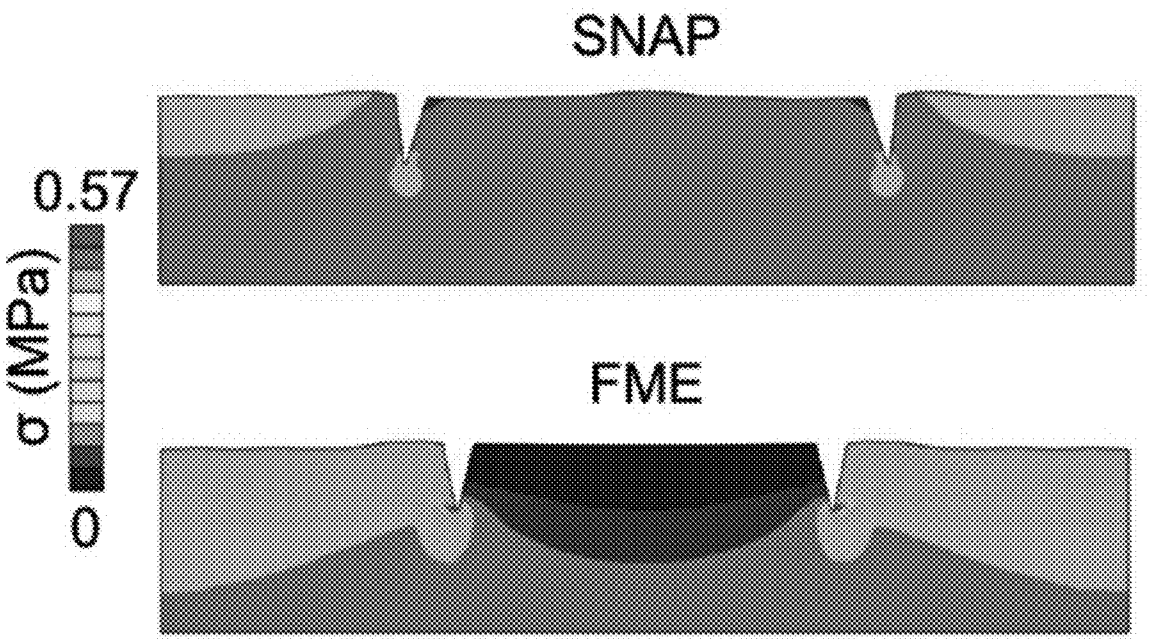

FEA results of FIG. 6E show considerably less stress in the surrounding tissue of the SNAP (0.22 MPa) compared to the FME (0.57 MPa), verifying that the SNAP may conform to tissue deformation and minimize tissue damage during dynamic motion.

Also, the excellent elasticity and conformability of the corresponding device prevents skin rash and irritation by reducing the stress on the skin tissue compared to the conventional non-stretchable flexible microneedle electrode (FIG. 6E) and may perform EP signal measurement without degradation in quality even after attachment for more than 7 days.

Figure 6F:
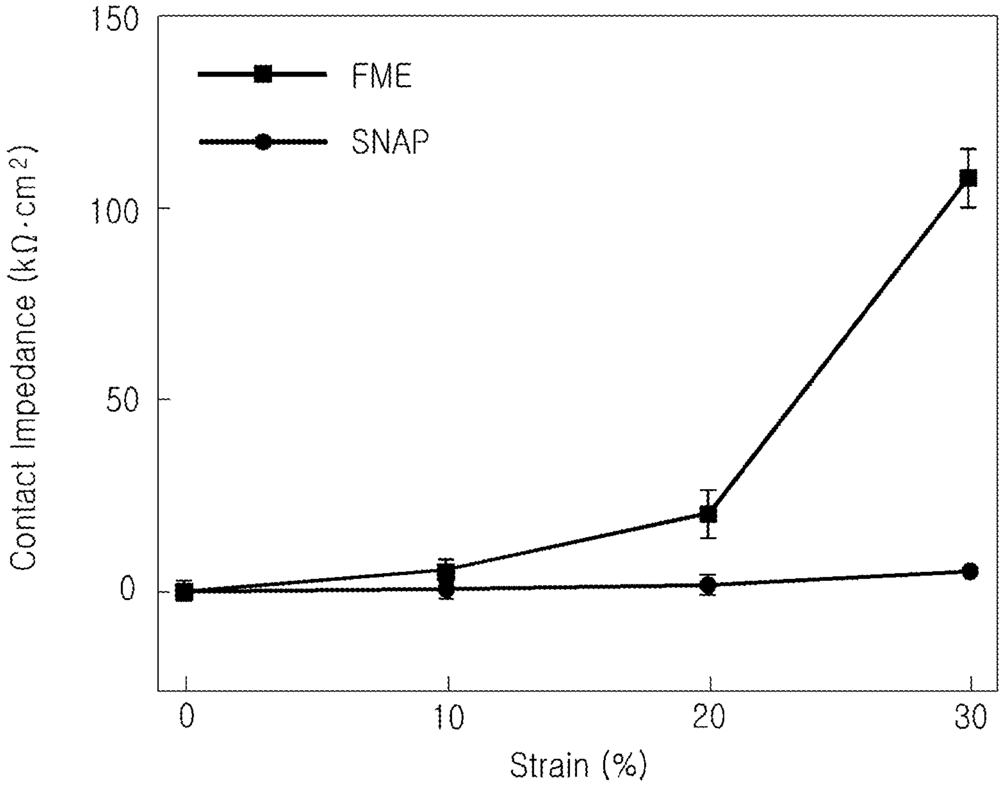

FIG. 6F is a graph showing measurement of skin contact impedance of the SNAP and the FME at varying tensile strain. Experimental results of skin contact impedance under skin strain indicate that adapting and intimate tissue interfacing of the SNAP reduces the likelihood of generating a physical gap between the electrode and the skin, facilitating maintenance of stable skin contact impedance with a minimal increase (increase of contact impedance <5 kohm·cm$^2$ at applied strain of 30%).

Figure 6G:
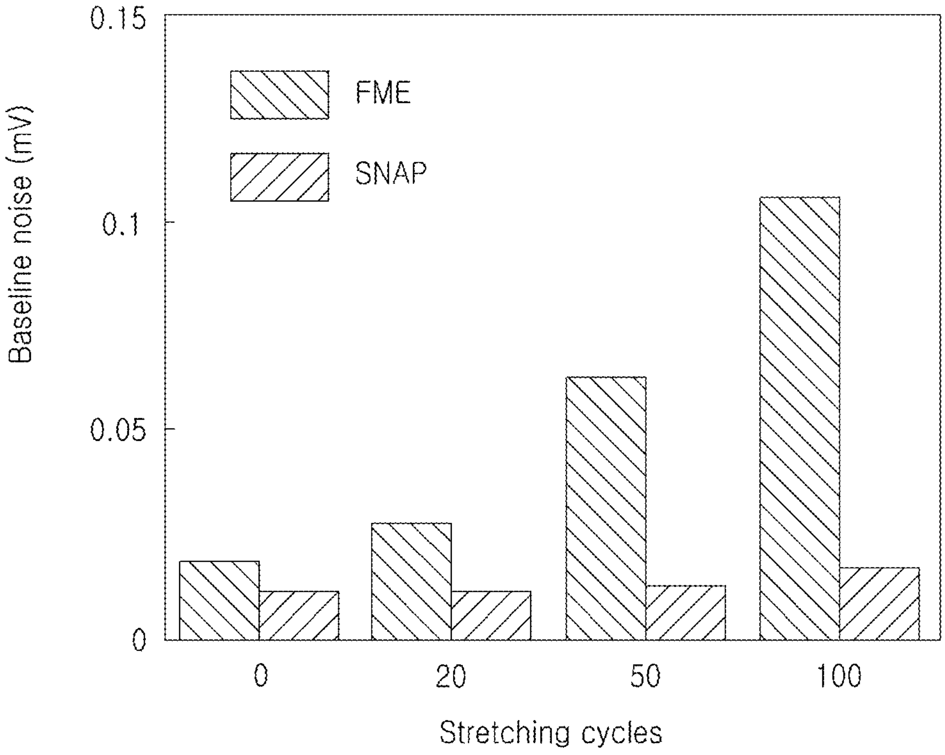

FIG. 6G is a graph comparing baseline noise levels of EMG signals measured using the SNAP and the FME during cyclic stretching and releasing.

To ensure electrical performance and mechanical compliance of the SNAP for long-term use, EMG baseline noise was monitored while the electrode was attached to the skin under repeated cyclic deformation. FIG. 6G shows that the SNAP maintains consistent EBG baseline noise even after 100 cycles of repeated 30% stretching and compressing at an attachment site. Through this, robust interface of the SNAP with the skin during dynamic motion may be confirmed.

Figure 6H:
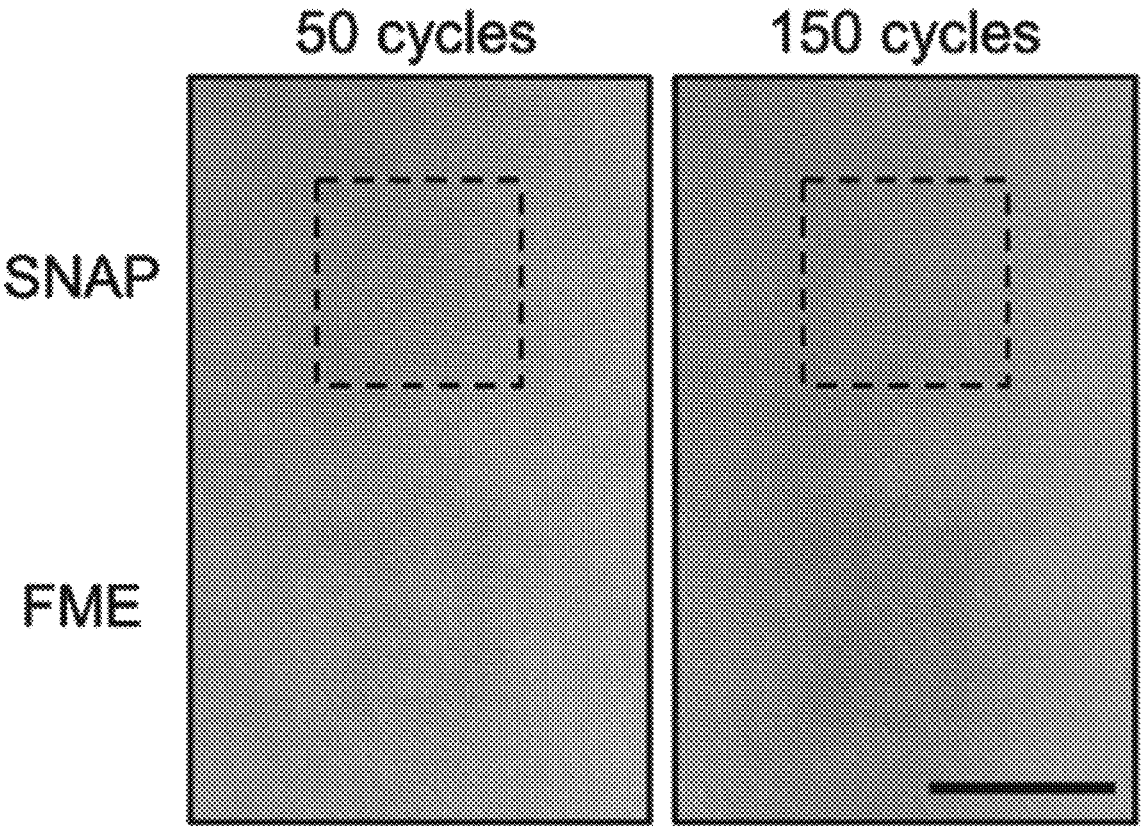

FIG. 6H illustrates optical images of the skin surface after cyclic stretching and releasing using the SNAP and the FME (left, after 50 cycles; right, after 150 cycles).

For 150 cycles of 30% stretching and releasing, the skin tissue interface of the SNAP does not cause noticeable red rashes, in contrast to the skin interface applied to the FME that exhibits visible skin redness under the same condition (FIG. 6H).

Figure 6I:
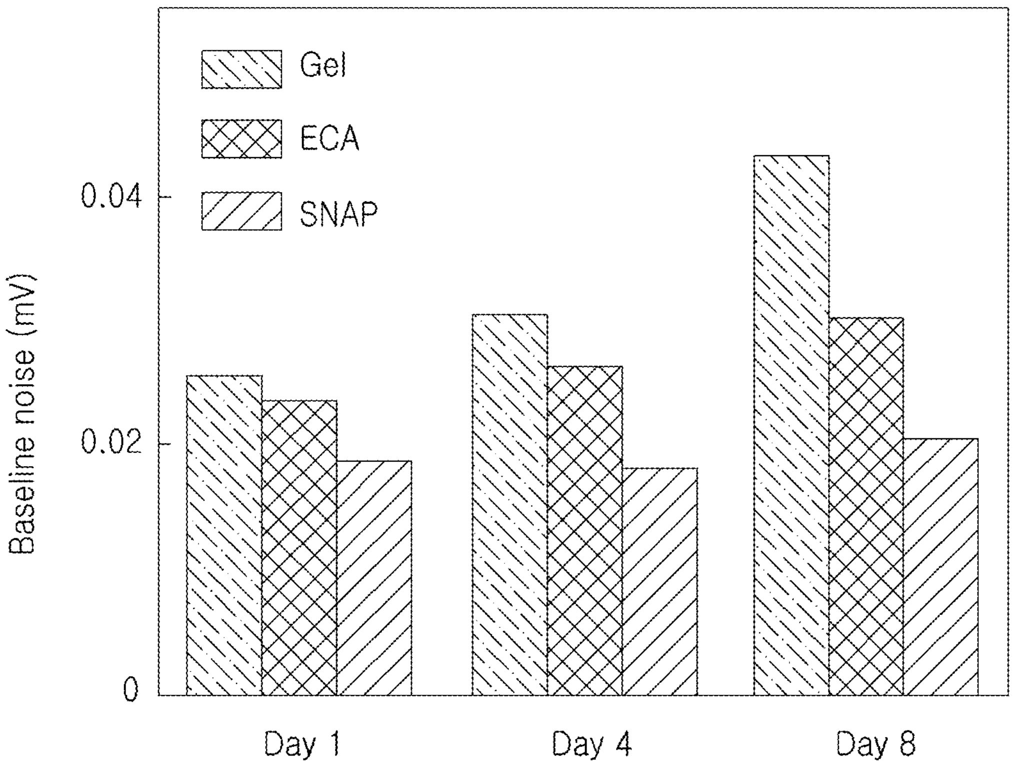

FIG. 6I is a graph comparing baseline noise levels of resting EMG signals measured using the SNAP, ECA, and commercial gel electrode for 8 days.

To assess the long-term wearability of the SNAP, the SNAP was attached to the forearm (target muscle: flexor carpi radialis) and a change in EMG baseline noise was monitored over 8 days. The results were compared to results obtained using the ECA electrode and the commercial gel electrode (TYH-WF25RP, Skyforever). During the 8-day measurement period, the output signal of the SNAP and the ECA electrode remained stable, with minimal change in baseline noise value (<10%). In contrast, the commercial gel electrode showed a notable increase in baseline noise (69% increased from day 1 to 8) due to electrode drying. While it is recommended to clean the skin using water or an alcohol swab to reduce the risk of infection during initial attachment of the SNAP, the results collectively demonstrate that the SNAP has unique capability of enabling robust, long-term monitoring EP signals regardless of the skin condition and deformation.

Figure 7:
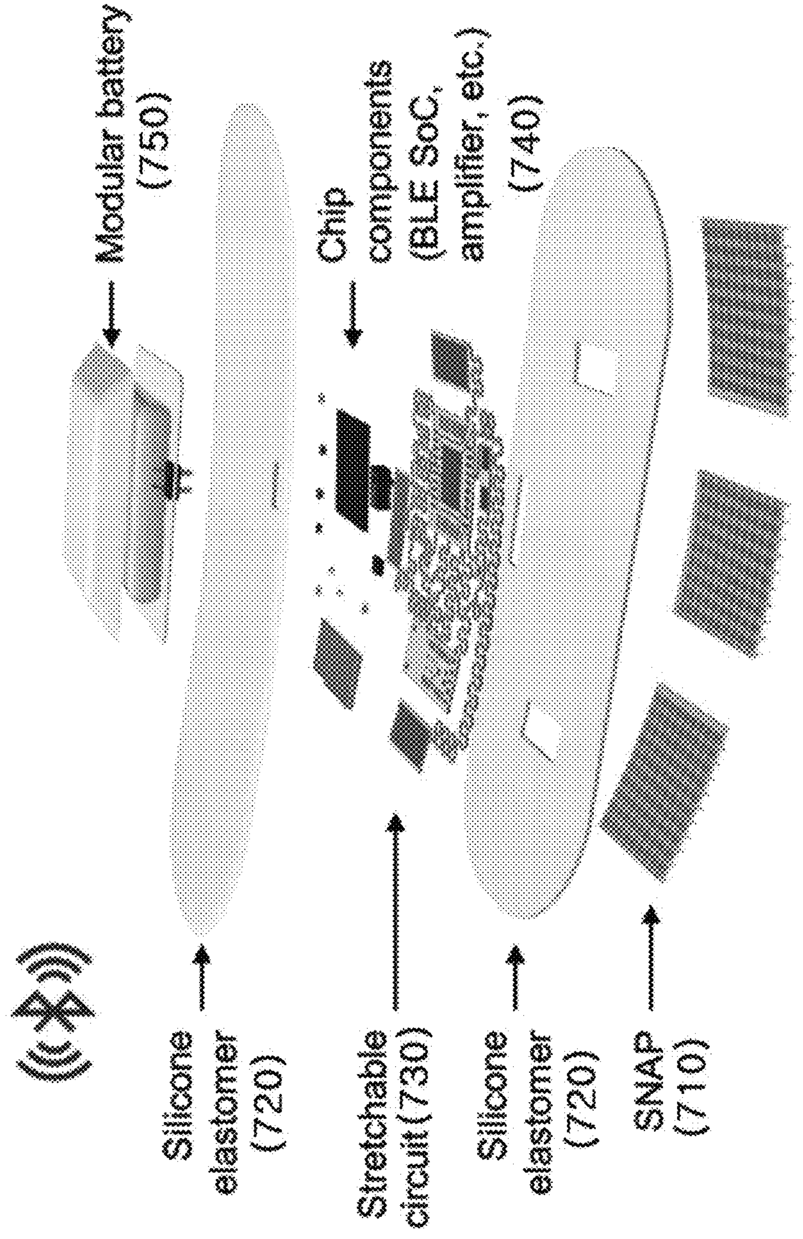
FIG. 7 illustrates a configuration of a wireless SNAP system according to an example embodiment.

FIG. 7 illustrates a configuration of a wireless SNAP system according to an example embodiment.

The wireless SNAP system includes a SNAP 710 surrounded by a silicone elastomer 720, a stretchable electronic circuit 730 surrounded by the silicone elastomer 720, a chip component (e.g., Bluetooth low-energy system-on-chip (BLE SoC), amplifier) 740, and a modular battery 750. Here, a low modulus silicone elastomer is only an example and various stretchable substrates may be used.

In the wireless SNAP system according to an example embodiment, the SNAP 710 surrounded by the silicone elastomer 720 is attached to a user's skin and obtains an EP signal. When the obtained EP signal is transmitted to the stretchable electronic circuit 730 surrounded by the silicone elastomer 720, the stretchable electronic circuit 730 performs real-time multichannel EP signal monitoring using a user interface application program through the chip component 740, for example, BLE SoC.

FIG. 7 proposes the wireless SNAP system that integrates the SNAP 710 and a stretchable wireless EP signal processing circuit, that is, the stretchable electronic circuit 730, and enables reliable EMG sensing during dynamic motion of the user. The flexible nature of the wireless SNAP system allows reliable EP signal recording in a target curvilinear muscle area, such as upper limb and lower limb. Also, a wireless function of the device eliminates the need for inconvenient wired setup of the conventional device.

In the SNAP according to an example embodiment, the serpentine structure of interconnects (e.g., 50 μm/36 μm/50 μm PI/Cu/PI structure) allows stretchability of the device with the integrated chip component 740 that includes the BLE SoC and the amplifier chip. The BLE SoC facilitates wireless communication with a portable electronic device (e.g., smartphone), allowing real-time multichannel EP signal monitoring through a user-friendly interface application program. To ensure optimal comfort and usability, the wireless SNAP system is encapsulated in the silicone elastomer (e.g., 750 μm thick; 69 kPa; Ecoflex 00-30) 720, providing a skin-like softness and high compliance to the tissue deformation, particularly, during bending and stretching of a target muscle region. Power of the device according to an example embodiment is provided with the modular battery 750, for example, a modular lithium polymer (LiPo) battery, which connects to the stretchable electronic circuit 730 of the wireless SNAP system through a metal pin connector. Here, the modular lithium polymer battery is only an example and various small batteries are available, including a coin cell battery and other types of lithium batteries.

Also, a metal opening on the bottom of the stretchable electronic circuit 730 of the wireless SNAP system provides an electrical connection to the SNAP system via an anisotropic conductive film cable and a magnetic connector to allow semi-permanent use of a circuit and easy replacement of the SNAP.

Figure 8:
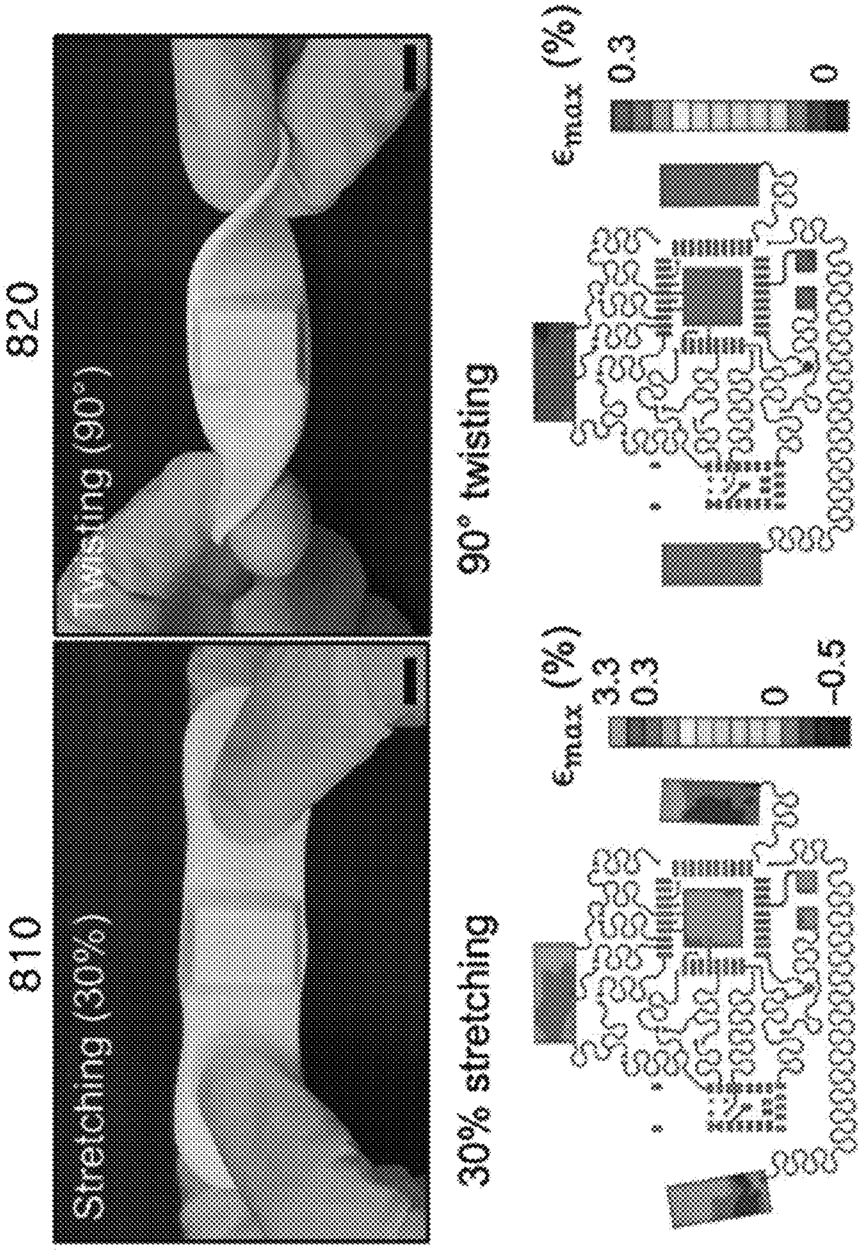
FIG. 8 illustrates mechanical endurance of a wireless SNAP system according to an example embodiment.

FIG. 8 illustrates mechanical endurance of a wireless SNAP system according to an example embodiment.

FIG. 8 illustrates photographs of the device captured during stretching (ε=30%) 810 and twisting (torsion of) 90° 820. FIG. 8 shows an example of a real image of the completed wireless SNAP system and demonstrates mechanical compliance of the SNAP system during dynamic deformation.

Figure 9:
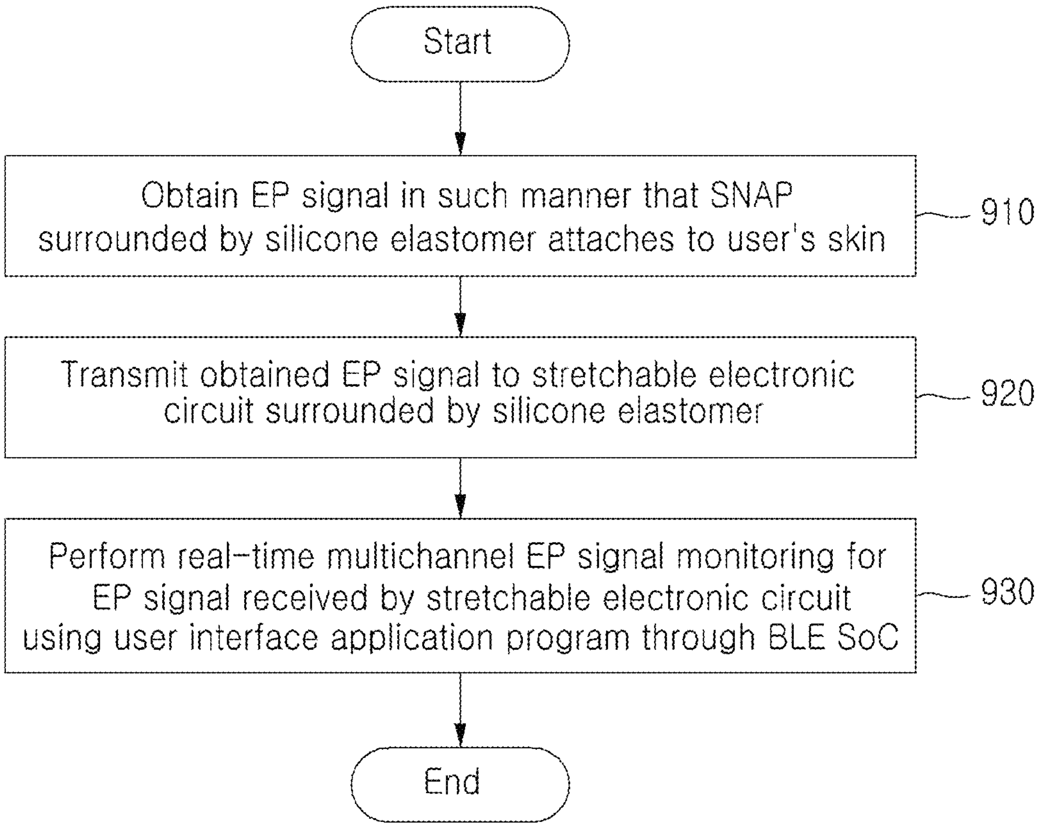
FIG. 9 is a flowchart illustrating an operating method of a wireless SNAP system according to an example embodiment.

FIG. 9 is a flowchart illustrating an operating method of a wireless SNAP system according to an example embodiment.

The operating method of the wireless SNAP system according to an example embodiment includes operation 910 of obtaining an EP signal in such a manner that a SNAP surrounded by a silicone elastomer attaches to a user's skin; operation 920 of electrically connecting to the SNAP for analysis of the obtained EP signal and transmitting the EP signal to a stretchable electronic circuit surrounded by the silicone elastomer; and operation 930 of performing real-time multichannel EP signal monitoring for the EP signal received by the stretchable electronic circuit using a user interface application program through a chip component including a BLE SoC and an amplifier.

According to an example embodiment, power is supplied to the SNAP system through a modular lithium polymer (LiPo) battery connected to the stretchable electronic circuit through a metal pin connector.

According to an example embodiment, a metal opening on the bottom of the stretchable electronic circuit provides an electrical connection to the SNAP system via an anisotropic conductive film cable and a magnetic connector to allow semi-permanent use of a circuit and replacement of the SNAP.

According to an example embodiment, it is possible to provide dynamic compliance to bending and stretching during the user's skin tissue deformation in the process of attaching to the user's skin and obtaining the EP signal by surrounding the SNAP and the stretchable electronic circuit of the SNAP system through the silicone elastomer.

According to an example embodiment, the chip component including the BLE SoC and the amplifier may support closed-loop control of an exoskeleton robot through real-time multichannel EP signal monitoring and communication with a control unit using a user interface application program using Bluetooth-based wireless communication.

Figure 10:
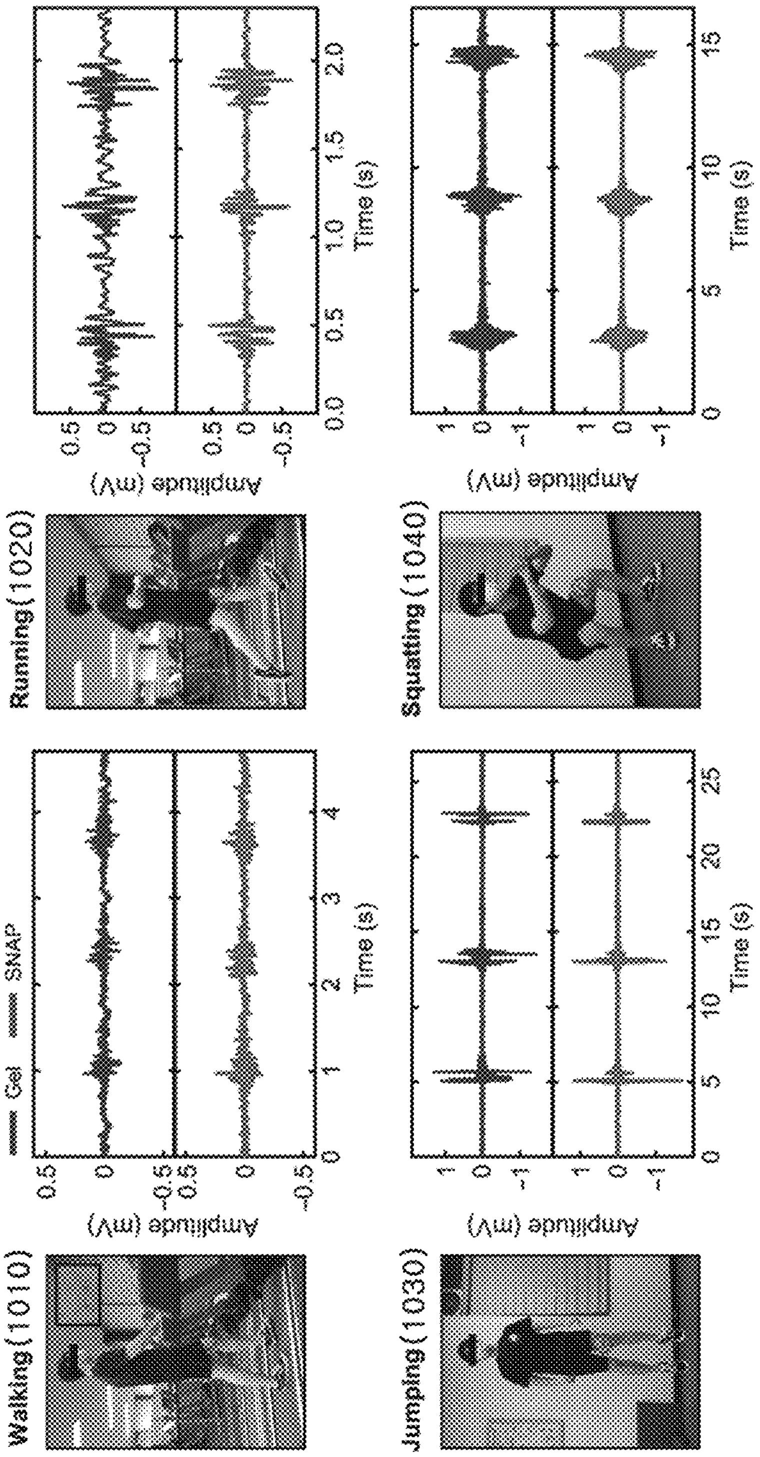
FIG. 10 illustrates electromyogram (EMG) monitoring performance of a wireless SNAP system among various ambulatory exercise according to an example embodiment.

FIG. 10 illustrates EMG monitoring performance of a wireless SNAP system among various ambulatory exercise according to an example embodiment.

The FEA simulation presented in FIG. 10 demonstrates the wireless SNAP system's ability to maintain the maximum principal strain of Cu interconnect trace (3.3%) below the fracture threshold (fracture strain of Cu≈5%) across all regions where components are under deformation. Note that most regions undergo substantially less strain (<0.3%) compared to the maximum strain. This confirms the wireless SNAP system's ability to maintain its structural integrity during operation in a dynamic environment.

To evaluate potential utility of the wireless SNAP system for EP recording during intense physical activity, EMG signals were monitored while attaching the device to the muscle of human thigh (target muscle: vastus medialis) during exercise. To simulate the dynamic condition caused by skin deformation and skin secretion during exercise, oil and baby powder were applied on an EP signal monitoring site. Then, EMG signals obtained with the wireless SNAP system were compared to those obtained with a wireless device integrated with the conventional gel electrode.

FIG. 10 provides examples of various ambulatory exercise, including walking 1010, running 1020, jumping 1030, and squatting 1040, along with their respective EMG measurements. In the case of light physical activity such as walking 1010, the influence of motion artifacts is not notable and no considerable difference is observed in EMG signals measured with the SNAP and the gel electrode. However, in the case of strenuous exercise, such as running 1020 and jumping 1030, the movement of a leg exposes the attached wireless devices (integrated with the SNAP and the gel electrode) to substantial acceleration, tremor, and tissue deformation. Measurement results of running 1020 and jumping 1030 show that the wireless SNAP system causes minimal baseline wandering and motion artifacts during running or jumping, while the gel electrode system exhibits noticeable fluctuation in EMG signals.

Figure 11:
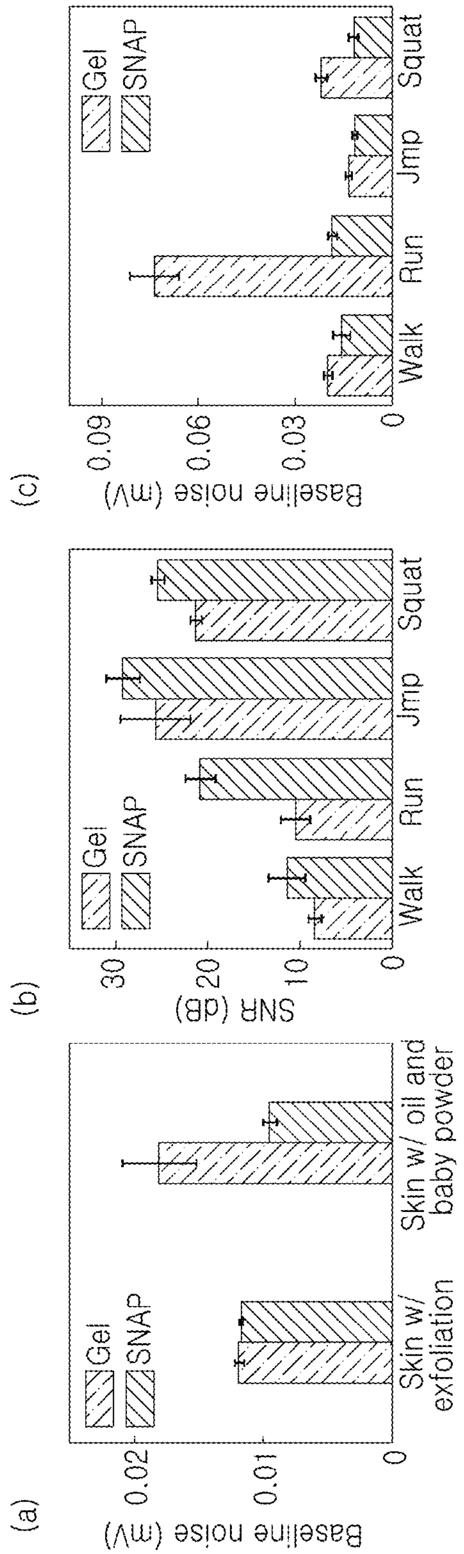
FIG. 11, (a), (b), and (c), are graphs showing EMG signal quality of a wireless SNAP system according to an example embodiment.

FIG. 11, (a), (b), and (c), are graphs showing EMG signal quality of a wireless SNAP system according to an example embodiment.

(a) of FIG. 11 is a graph showing baseline noise amplitudes of both pretreated skin condition and contaminated skin condition, (b) of FIG. 11 is a graph showing SNR values, and (c) of FIG. 11 is a graph of EMG signal quality recording including baseline noise amplitudes in four types of ambulatory motion.

EMG signal quality of the wireless SNAP system significantly reduces baseline noise (47% lower than the gel electrode, 73% lower than the ECA electrode), and shows robust performance regardless of the skin condition, demonstrating that the proposed device may withstand skin contamination. This trend was observed not only in EMG but also consistently in other EP signals, such as electroencephalogram, which has much lower signal amplitudes. The overall results presented here provide strong evidence of the wireless SNAP system's ability to offer high-quality EP signal measurement under dynamic motion and also suggest its potential for diverse applications in health care, athlete training, musculoskeletal rehabilitation, and HMI.

FIGS. 12A to 12D illustrate experimental results of a wireless SNAP system as a human-machine interface (HMI) according to an example embodiment.

EMG-based exoskeleton robot technology according to an example embodiment provides the advantage of rapidly recognizing user movement attempt, surpassing a conventional kinetic-based exoskeleton robot by 30 to 100 ms. Also, it is possible to integrate user input and feedback through neuromuscular connection. However, signal instability caused by a user's movement and skin secretion poses challenge to the practical use of EMG-based assistive robot control. In addition, a cumbersome wired sensor system requires extensive setup time and restricts the user's natural movement range, confining the exoskeleton robot's application to laboratory settings.

An example embodiment presents an exoskeleton robot control using the preparation-free, low-profile, and wireless SNAP system to be applied to intelligent neuroprosthetics, physical motion assistance, and other HMI fields.

Figure 12A:
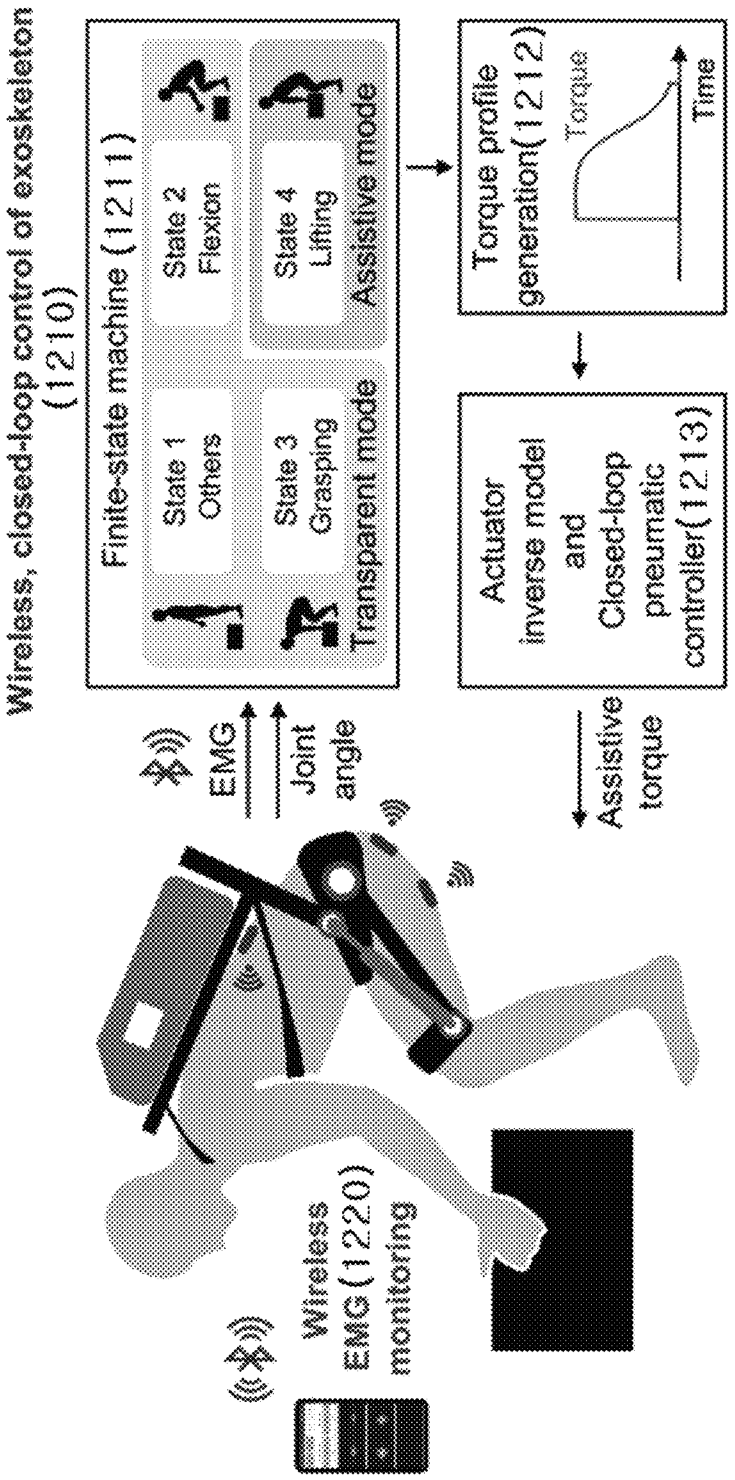
FIGS. 12A to 12D illustrate experimental results of a wireless SNAP system as a human-machine interface (HMI) according to an example embodiment.
Figure 12B:
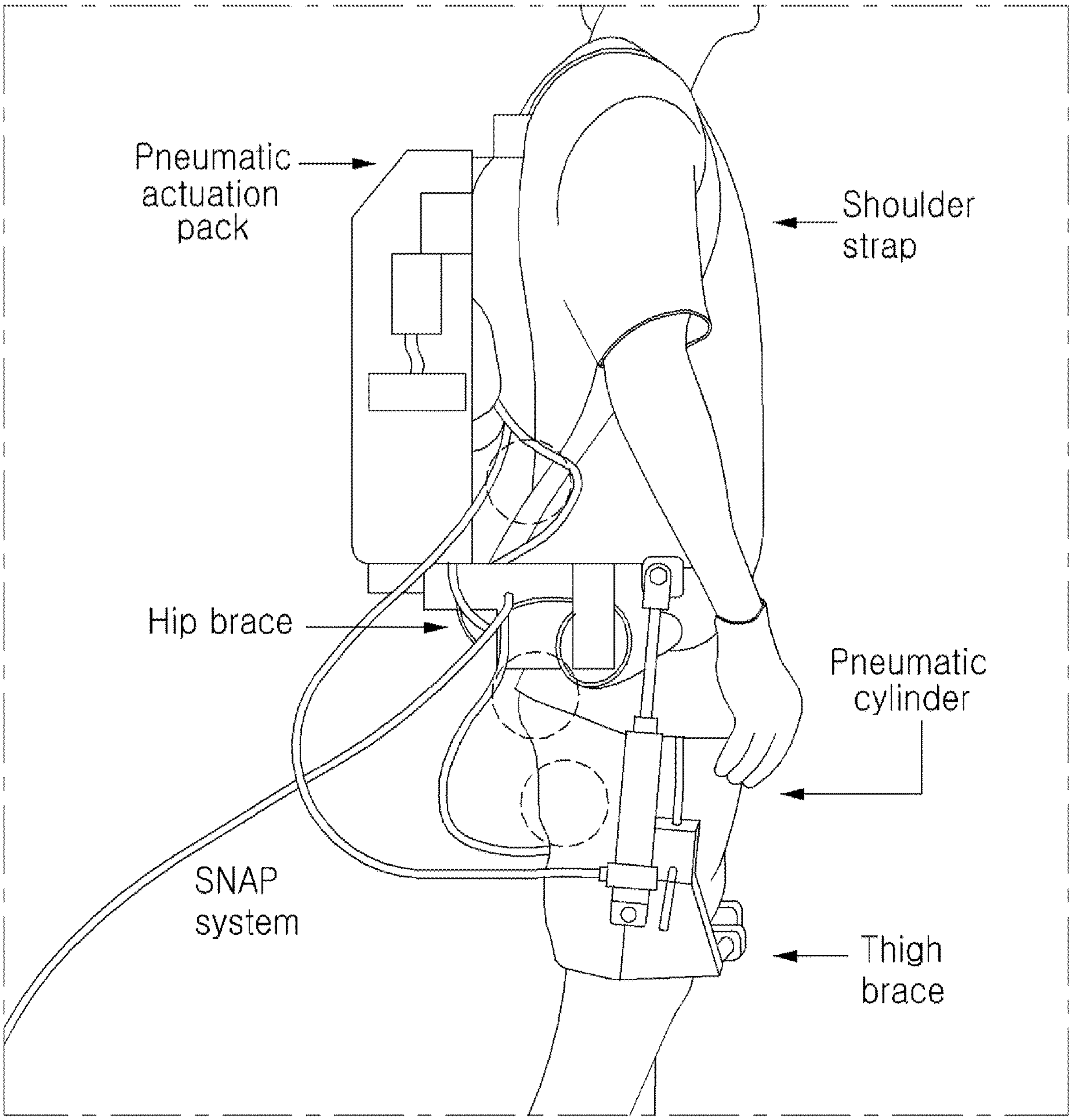

An example embodiment demonstrates a wireless EMG-triggered closed-loop control of a back-supporting robot designed for lifting load using the SNAP system and serving as the back. FIGS. 12A and 12B provide robotic assistance strategy and a system configuration using the wireless SNAP system.

FIG. 12A depicts a system architecture and control strategy of an exoskeleton robot. The SNAP system attached to lower limb muscle wirelessly transmits an EMG signal to an exoskeleton robot controller to trigger an assistance operation. Another SNAP system attached to the back muscle monitors muscle activity to evaluate the robotic assistance performance.

FIG. 12B illustrates a hardware configuration of a pneumatic back support exoskeleton system. Linear actuation of a pneumatic cylinder caused the device to push the trunk, generating an assistive hip joint torque for lifting heavy external load.

Figure 12C:
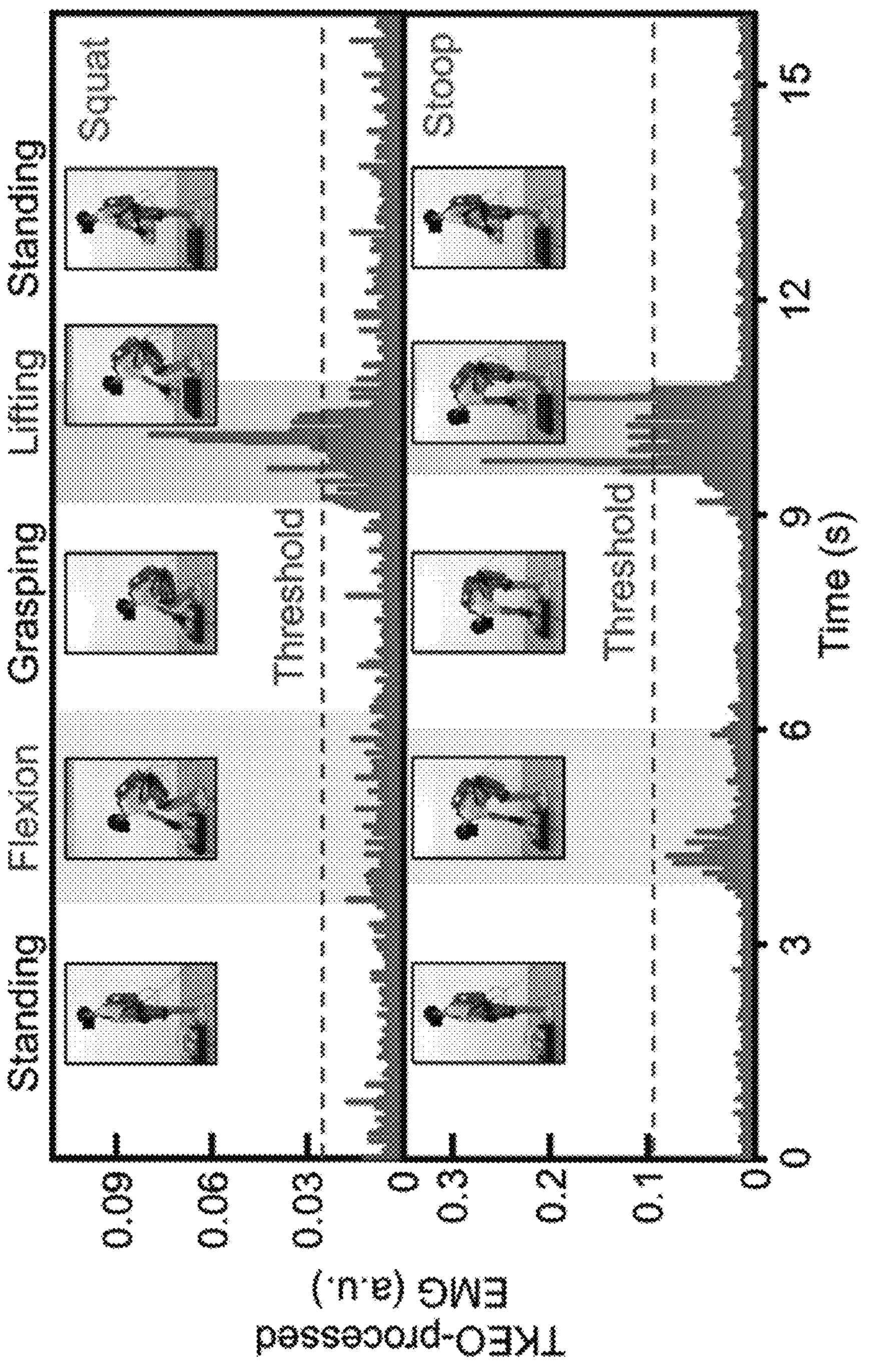

FIG. 12C illustrates real-time measurement results of TKEO-EMG signals from the trigger muscle during a single cycle of squat lifting and stoop lifting.

Referring again to FIG. 12A, EMG signals are monitored through the SNAP system attached to lower limb muscle (target muscle: gluteus maximus (GM) for squat lifting, biceps femoris (BF) for stoop lifting) and when the EMG signals exceed a preset threshold, an assistive robot operates.

The SNAP system provides excellent immunity to skin perspiration and deformation compared to the conventional gel electrode and provides a robust sensing interface during a dynamic HMI operation (1210). Collected EMG signals are transmitted to a finite state machine of a microcontroller unit and rectified by Teager-Kaiser Energy Operator (TKEO), determining a current state of the exoskeleton robot to determine whether it is in an assistive mode (1211). This process generates a corresponding torque profile (1212). The assistive torque is conveyed to a hip joint of the user through a closed-loop pneumatic controller, using desired pneumatic pressure obtained from an actuator inverse model (1213). This assistive strategy prevents musculoskeletal disorder by reducing muscle overexertion and fatigue resulting from repetitive lifting of heavy loads. Also, an additional wireless SNAP system is attached to the back muscle in which the target muscle is located. This system communicates with a smartphone to evaluate the performance of the exoskeleton robot by analyzing a reduction in root mean square of EMG (RMS EMG) (1220).

FIG. 12C presents the proof-of-concept demonstration of assistive capability of the exoskeleton robot integrated with the wireless SNAP system for closed-loop control, and shows lifting of 10-kg-load. The experiments encompassed scenarios involving both pretreated skin and non-pretreated, perspiring skin conditions, aiming to evaluate the performance of the SNAP system in scenarios that require no prior preparation.

Figure 12D:
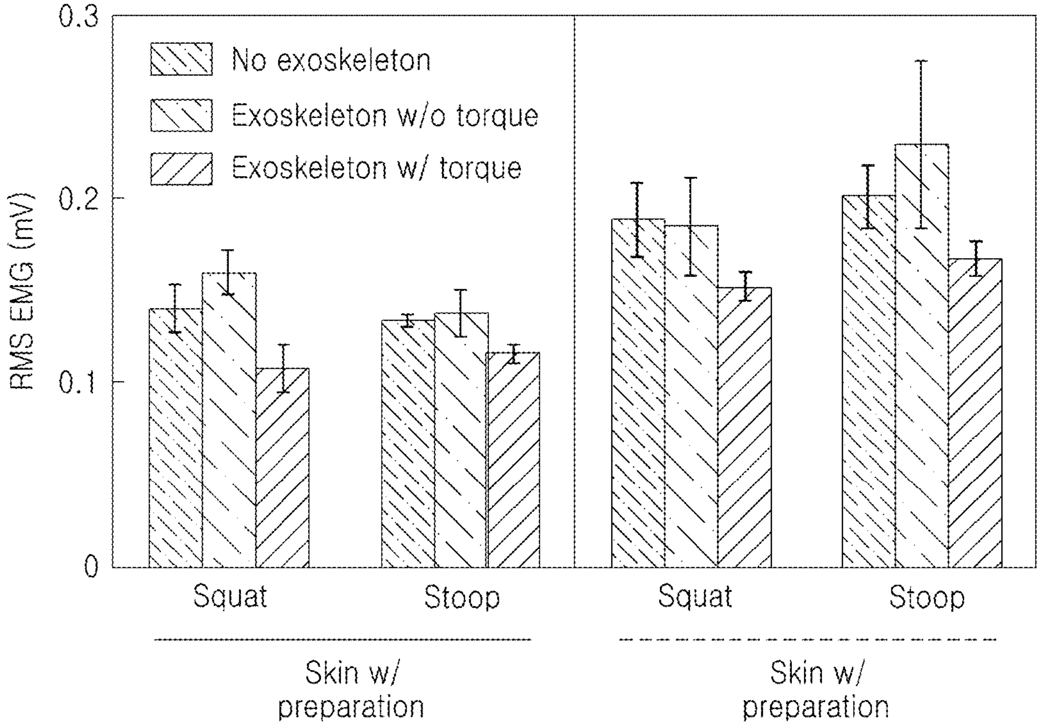

FIG. 12D is a graph for comparison of RMS EMG with and without robot assistance.

RMS EMG results measured from L1 muscle showed a notable decrease of muscle activation (18.1% in both pretreated skin and non-pretreated, perspiring skin condition on average), when compared to a case without robotic assistance. The results indicate that the SNAP system effectively addresses challenges related to unstable EMS recordings due to the user's movement skin secretion, which have traditionally impeded EMG-based exoskeleton robot control. Furthermore, the exoskeleton robot equipped with the SNAP system exhibits positive impact on muscle fatigue, underscoring its potential to improve functional mobility for individuals requiring assistance in lifting heavy objects. Comprehensively, integration of a preparation-free, wireless EP signal monitoring system into an assistive exoskeleton robot presents a promising solution for HMIs, particularly, in the wireless prosthetic control field, contributing to physical human augmentation.

As described above, the SNAP according to an example embodiment may be applied to a healthcare application that provides feedback by stably measuring and analyzing EP signals of a human for a long term.

Also, the SNAP according to an example embodiment is applied to a human-machine interface (HMI) to minimize noise due to a wearer's skin condition and movement and is optimized for an application that requires an accurate signal acquisition and motion recognition function.

Also, the SNAP according to an example embodiment may be used for various transdermal-based treatments, such as electrical stimulation, through attachment to the skin for a long period of time without inflammation.

Also, the SNAP according to an example embodiment may be used not only in a wearable device but also in a bio-implantable device through application to various bio-implantable multichannel electrical signal measurement and stimulation, such as cerebral cortical conduction and nerve conduction.

The SNAP according to an example embodiment may effectively reduce a complex skin preparation time, such as removing skin hair, exfoliating, and applying conductive gel, and may also perform high-quality EP signal measurement. Therefore, significant demand is expected in various medical, rehabilitation, and industrial EP signal-based wearable robot fields that require a short preparation time and high-quality wearability.

The SNAP is capable of performing stable high-quality EP signal measurement for more than a week and, at the same time, exhibits high biocompatibility. Therefore, the SNAP is expected to be highly competitive in the digital healthcare and medical field that requires accurate acquisition of biosignals for a long period of time without causing the wearer's discomfort.

According to example embodiments, it is expected to create a highly industrial added value in that EP signal sensor technology important for feedback linkage with a medical rehabilitation wearable robot and prosthetics while the demand for rehabilitation engineering is increasing due to aging population. Also, the present invention is expected to have high demand from industrial companies that require high usability and time reduction in that high-quality biosignal measurement with simple attachment is possible without a special additional preparation process. Also, in the future, the prospect for introducing the present technology is expected to be bright in that, when applied to a wearable device, a stable long-term operation is possible and monitoring EP signals with high biocompatibility is possible.

The apparatuses described herein may be implemented using hardware components, software components, and/or combination of the hardware components and the software components. For example, a processing device and components described herein may be implemented using one or more general-purpose or special purpose computers, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that the processing device may include multiple processing elements and/or multiple types of processing elements. For example, the processing device may include multiple processors or a processor and a controller. In addition, other processing configurations are possible, such as parallel processors.

The software may include a computer program, a piece of code, an instruction, or at least one combination thereof, for independently or collectively instructing or configuring the processing device to operate as desired. Software and/or data may be embodied in any type of machine, component, physical equipment, virtual equipment, computer storage medium or device, to provide instructions or data to the processing device or be interpreted by the processing device. The software also may be distributed over network coupled computer systems so that the software is stored and executed in a distributed fashion. The software and data may be stored by one or more computer readable storage mediums.

The methods according to example embodiments may be implemented in a form of a program instruction executable through various computer methods and recorded in non-transitory computer-readable media. The media may include, alone or in combination with program instructions, a data file, a data structure, and the like. The program instructions recorded in the media may be specially designed and configured for the example embodiments or may be known to those skilled in the computer software art and thereby available. Examples of the media include magnetic media such as hard disks, floppy disks, and magnetic tapes; optical media such as CD ROM and DVD; magneto-optical media such as floptical disks; and hardware devices that are specially configured to store and perform program instructions, such as read-only memory (ROM), random access memory (RAM), flash memory, and the like. Examples of program instructions include a machine code as produced by a compiler and an advanced language code executable by a computer using an interpreter.

Although the example embodiments are described with reference to some specific example embodiments and accompanying drawings, it will be apparent to one of ordinary skill in the art that various alterations and modifications in form and details may be made in these example embodiments without departing from the spirit and scope of the claims and their equivalents. For example, suitable results may be achieved if the described techniques are performed in different order, and/or if components in a described system, architecture, device, or circuit are combined in a different manner, and/or replaced or supplemented by other components or their equivalents.

Therefore, other implementations, other example embodiments, and equivalents of the claims are to be construed as being included in the claims.

What is claimed is:

1. A stretchable microneedle adhesive patch (SNAP) comprising:

an electrically conductive adhesive (ECA) layer configured to attach to a user's skin to obtain an electrophysiological (EP) signal regardless of the user's skin condition;

a microneedle sensor including a microneedle array configured to penetrate the stratum corneum by passing through the ECA layer and to directly contact the skin epidermis of the user; and conductive wire-based stretchable interconnects having a serpentine structure that is electrically and mechanically connected to the microneedle sensor to dynamically adapt to skin deformation of the user, wherein the ECA layer is configured to enhance an electrical interface between the microneedle sensor and the user skin by providing an additional electrical conductive path to the user's skin around the microneedle sensor and by lowering skin contact impedance between the microneedle sensor and the user's skin.

2. The SNAP of claim 1, wherein the ECA layer is configured to simultaneously provide electrical conductivity and skin adhesion through silicone-based electrical conductive adhesives coating the conductive wire-based stretchable interconnects and the microneedle sensor and to implement low impedance between the microneedle sensor and the user's skin.

3. The SNAP of claim 1, wherein the microneedle sensor is configured to integrate a gold-coated silicon microneedle array under the conductive wire-based stretchable interconnects, and to allow the gold-coated silicon microneedle array to penetrate into the stratum corneum of the user and to directly contact the skin stratum corneum without reaching a pain receptor.

4. The SNAP of claim 1, wherein the microneedle sensor is configured to form a microneedle array through partial dicing and isotropic wet etching of a silicon (Si) wafer, followed by deposition of titanium (Ti) and gold (Au), and individually isolated microneedles are generated through wet etching while coating electrically conductive adhesives on the front of a gold-coated silicon microneedle array and then protecting a lower portion of the microneedle array with the deposited gold and wax applied to sides of the microneedle, and the isolated microneedle array is generated through integration with the electrically and mechanically connected stretchable interconnects using conductive epoxy.

5. The SNAP of claim 1, wherein the conductive wire-based stretchable interconnects are in a form in which conductive wires are integrated on a stretchable substrate, and are configured to transfer obtained EP signals to a circuit unit for analysis of the EP signals through electrical connection to the microneedle sensor.

6. The SNAP of claim 1, wherein the conductive wire-based stretchable interconnects are in a form in which conductive wires are integrated on a stretchable substrate, and are configured to dynamically accommodate deformation of the user's skin through a serpentine structure and to provide elasticity and comfortable long-term wearability.

7. The SNAP of claim 1, wherein the SNAP is configured to provide adhesion through the microneedle sensor and the ECA layer having a modulus similar to that of the user's skin tissue and to provide elasticity through the conductive wire-based stretchable interconnects, preventing detachment of the SNAP, and to reduce stress on the user's skin tissue to prevent skin rash and irritation and to perform EP signal measurement without quality degradation even after long-term attachment.

8. A stretchable microneedle adhesive patch (SNAP) system comprising:

a SNAP of claim 1, configured to attach to a user's skin and to be surrounded by a stretchable substrate that obtains an electrophysiological (EP) signal;

a stretchable electronic circuit configured to electrically connect to the SNAP for analysis of the obtained EP signal, to receive the EP signal, and to be surrounded by the stretchable substrate; and a chip component including a wireless low-energy system-on-chip (SoC) and an amplifier configured to perform real-time multichannel EP signal monitoring for the EP signal received by the stretchable electronic circuit using a user interface application program.

9. The SNAP system of claim 8, further comprising:

a battery configured to connect to the stretchable electronic circuit through a metal pin connector and to supply power to the SNAP system, wherein a metal opening on the bottom of the stretchable electronic circuit provides an electrical connection to the SNAP system via an anisotropic conductive film cable and a magnetic connector to allow semi-permanent use of a circuit and replacement of the SNAP.

10. The SNAP system of claim 8, wherein the stretchable substrate is configured to provide dynamic compliance to bending and stretching during the user's skin tissue deformation in the process of attaching to the user's skin and obtaining the EP signal by surrounding the SNAP and the stretchable electronic circuit of the SNAP system.

11. The SNAP system of claim 8, wherein the ECA layer is configured to simultaneously provide electrical conductivity and skin adhesion through silicone polymer-based electrical conductive adhesives coating the conductive wire-based stretchable interconnects and the microneedle sensor and to implement low impedance between the microneedle sensor and the user's skin.

12. The SNAP system of claim 8, wherein the microneedle sensor is configured to integrate a gold-coated silicon microneedle array under the conductive wire-based stretchable interconnect, and to allow the gold-coated silicon microneedle array to penetrate into the stratum corneum of the user and to directly contact the skin stratum corneum without reaching a pain receptor.

13. The SNAP system of claim 8, wherein the conductive wire-based stretchable interconnects are in a form in which conductive wires are integrated on a stretchable substrate, and are configured to transfer obtained EP signals to a stretchable circuit unit for analysis of the EP signals through electrical connection to the microneedle sensor and to dynamically accommodate deformation of the user's skin through a serpentine structure and to provide elasticity and comfortable long-term wearability.

14. The SNAP system of claim 8, wherein the chip component including the wireless low-energy SoC and the amplifier is configured to support closed-loop control of an exoskeleton robot through real-time multichannel EP signal monitoring and communication with a control unit using a user interface application program using Bluetooth-based wireless communication.

15. An operating method of a stretchable microneedle adhesive patch (SNAP) system, the method comprising:

obtaining an EP signal in such a manner that a SNAP of claim 1 surrounded by a stretchable substrate attaches to a user's skin;

electrically connecting to the SNAP for analysis of the obtained EP signal and transmitting the EP signal to a stretchable electronic circuit surrounded by the stretchable substrate; and performing real-time multichannel EP signal monitoring for the EP signal received by the stretchable electronic circuit using a user interface application program through a chip component including a wireless low-energy system-on-chip (SoC) and an amplifier.

16. The method of claim 15, wherein power is supplied to the SNAP system through a battery connected to the stretchable electronic circuit through a metal pin connector, and a metal opening on the bottom of the stretchable electronic circuit provides an electrical connection to the SNAP system via an anisotropic conductive film cable and a magnetic connector to allow semi-permanent use of a circuit and replacement of the SNAP.

17. The method of claim 15, wherein, through the stretchable substrate, dynamic compliance is provided to bending and stretching during the user's skin tissue deformation in the process of attaching to the user's skin and obtaining the EP signal by surrounding the SNAP and the stretchable electronic circuit of the SNAP system.

18. The method of claim 15, wherein, through the chip component including the wireless low-energy SoC and the amplifier, closed-loop control of an exoskeleton robot is supported through real-time multichannel EP signal monitoring and communication with a control unit using a user interface application program using Bluetooth-based wireless communication.

* * * * *